United States Patent [19]
Muchowski et al.

[11] 3,985,791
[45] Oct. 12, 1976

[54] 16-PHENOXY AND 16-SUBSTITUTED PHENOXY-PROSTATRIENOIC ACID DERIVATIVES

[75] Inventors: Joseph M. Muchowski, Mexico City, Mexico; John H. Fried, Palo Alto, Calif.

[73] Assignee: Syntex (U.S.A.) Inc., Palo Alto, Calif.

[22] Filed: Dec. 22, 1975

[21] Appl. No.: 643,219

Related U.S. Application Data

[63] Continuation-in-part of Ser. No. 589,218, June 23, 1975.

[52] U.S. Cl. .................. 260/473 A; 260/240 R; 260/293.65; 260/343.2 R; 260/345.7; 260/345.8; 260/346.2 R; 260/347.3; 260/347.4; 260/429.9; 260/438.1; 260/439 R; 260/448 R; 260/501.1; 260/501.11; 260/501.17; 260/520 B; 424/308; 424/317
[51] Int. Cl.² .......................................... C07C 69/76
[58] Field of Search .......... 260/473 A, 520 B, 501.1

[56] References Cited
UNITED STATES PATENTS

| | | | |
|---|---|---|---|
| 3,873,598 | 3/1975 | Crabbe et al. | 260/468 D |
| 3,879,438 | 4/1975 | Crabbe et al. | 260/468 D |

FOREIGN PATENTS OR APPLICATIONS

| | | | |
|---|---|---|---|
| 806,995 | 5/1974 | Belgium | 260/468 D |
| 2,505,303 | 8/1975 | Germany | 260/468 D |

OTHER PUBLICATIONS
Binder, D. et al., Prostaglandins, vol. 6, No. 1, Apr. 10, 1974, pp. 87–90.
Dawson, W. et al., Nature, vol. 250, July 26, 1974, pp. 331–332.
Annales de Biologie Animale Biochimie Biophysique, vol. 15, (2), pp. 161–174 and pp. 383–384.

*Primary Examiner*—Paul J. Killos
*Attorney, Agent, or Firm*—Gerard A. Blaufarb; William B. Walker

[57] ABSTRACT

Novel racemic and 8R-antimeric 16-phenoxy- and 16-(o, m or p)-substituted phenoxy derivatives of $9\alpha$, $11\alpha$,15-trihydroxy-17,18,19,20-tetranorprosta-4,5,13-trans-trienoic acids, which may be further substituted at C-15 by a methyl or ethyl group, the pharmaceutically acceptable, non-toxic lower alkyl esters and salts thereof and processes for the production of such compounds. dl $9\alpha,11\alpha,15\alpha$-trihydroxy-16-m-trifluoromethylphenoxy-17,18,19,20-tetranorprosta-4,5,13-trans-trienoic acid and dl $9\alpha,11\alpha,15$-trihydroxy-15-methyl-16-m-trifluoromethylphenoxy-17,18,19,20-tetranorprosta-4,5,13-trans-trienoic acid are representative compounds of the class. These compounds possess prostaglandin-like activities and thus are useful in the treatment of mammals where prostaglandins are indicated. They are particularly useful as luteolytic agents in female mammals.

48 Claims, No Drawings

16-PHENOXY AND 16-SUBSTITUTED PHENOXY-PROSTATRIENOIC ACID DERIVATIVES

This application is a continuation in part of U.S. application Ser. No. 589,218, filed June 23, 1975.

The present invention relates to certain novel prostaglandin analogs and to the process for the production thereof.

More particularly, the present invention relates to 16-phenoxy- and 16-(o, m or p)-substituted phenoxy derivatives of 9α,11α,15-trihydroxy-17,18,19,20-tetranorprosta-4,5,13-trans-trienoic acids, the 15ξ-methyl and ethyl derivatives thereof, as well as the pharmaceutically acceptable, non-toxic lower alkyl esters and salts thereof and to processes for producing such compounds.

Prostaglandins have classically been described as chemically related 20 carbon chain hydroxy fatty acids having the basic skeleton of prostanoic acid:

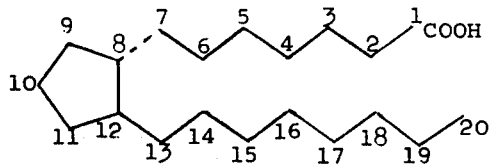

The prostaglandins having a hydroxyl group at the C-11 position and a keto group at the C-9 position are known as the PGE series, those having a hydroxyl group in place of the keto group are known as the PGF series and are further designated by an α or β suffix to indicate the configuration of the hydroxyl group at said position. The natural compounds are the α-hydroxy substituted compounds. They may contain different degrees of unsaturation in the molecule, particularly at C-5, C-13 and C-17, the unsaturation is also indicated by a suffix. Thus, for example, the PGF$_1$ and PGE$_1$ series refer to prostanoic acids having a trans olefin bond at the C-13 position, while the PGF$_2$ and PGE$_2$ series refer to prostadienoic acids having a cis-olefin bond at the C-5 position and a trans olefin bond at the C-13 position. For a review on prostaglandins and the definition of primary prostaglandins, see, for example, S. Bergström, *Recent Progress in Hormone Research* 22, pp. 153-175 (1966) and *Science* 157, page 382 (1967) by the same author.

The preparation of derivatives of prostanoic acid has become of great importance since the demonstration of the highly interesting range of biological and pharmacological activities of natural prostaglandins.

The great majority of these studies have focused on modification of the two side chains, or modifications of the substituents attached to the cyclopentane moiety (see for example U. Axen et al, *Synthesis* Vol. 1, John Wiley and Sons Inc., New York, N. Y. 1973 and P. H. Bently, *Chem. Soc. Reviews* 2, 29 (1973)). The synthesis of prostaglanin analogs having a diethylenic (allenic) unsaturation in the carboxylic acid chain has been described, among others, in U.S. Pat. No. 3,879,438, issued Apr. 22, 1975, of Crabbé and Fried. The synthesis of several prostaglandin analogs in which the alkyl chain attached to C-15 in the natural compounds is replaced by an aryloxymethyl group, and their activities have recently been reported [see, for example, D. Binder et al., *Prostaglandins* Vol. 6, No. 1 p. 87 (1974), M. Dukes et al., *Nature* Vol. 250, p. 30 (1974), U.S. Pat. No. 3,864,387 and Belgium Pat. No. 806,995.

In accordance with the present invention we have prepared certain novel 16-phenoxy-prostaglandin analogs represented by the following formula:

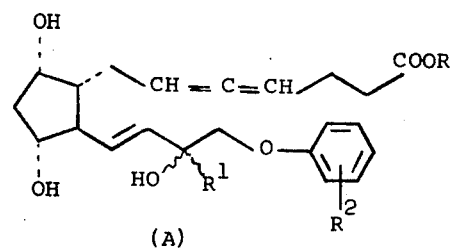

(A)

wherein R is hydrogen, a lower alkyl group of 1 to 4 carbon atoms, or the pharmaceutically acceptable, non-toxic salts of compounds in which R is hydrogen;

$R^1$ is hydrogen, methyl or ethyl; $R^2$ is hydrogen, o-, m- or p-halo (fluoro, chloro or bromo), o-, m- or p-trifluoromethyl, o-, m- or p-lower alkyl or o-, m- or p-lower alkoxy, and the wavy lines (ξ) indicate the α or β configuration, or mixtures thereof, provided that when $R^1$ is α the hydroxyl group, attached to the same carbon atom as $R^1$, is β, and when $R^1$ is β the hydroxyl group, attached to the same carbon atom as $R^1$, is α.

The dotted lines shown in the above formula and in the formulas below indicate that the substituents are in α configuration, i.e., below the plane of the cyclopentane ring.

The double bond at C-13 in the compounds of the present invention has the same configuration as in natural prostaglandins of the PGE and PGF series, that is the trans configuration.

These novel compounds possess asymmetric centers and thus can be produced as racemic mixtures or as individual 8R-antimers. The racemic mixtures can be resolved if desired at appropriate stages by methods known to those skilled in the art, to obtain the respective individual antimers. It is to be understood that the racemic mixtures and the individual 8R-antimers are encompassed within the scope of the present invention.

Thus, the racemic compounds of formula (A) in which the hydroxyl group at C-15 is in α-configuration are mixtures in equal proportions of compounds of the formulas:

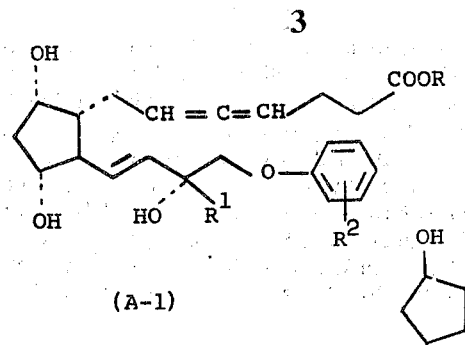

(A-1)

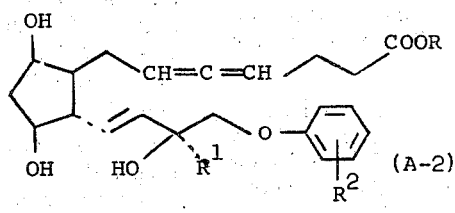

(A-2)

The racemic compounds of formula (A) in which the hydroxyl group at C-15 is in β-configuration are mixtures in equal proportions of compounds of the formulas:

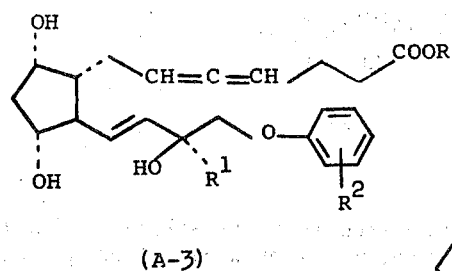

(A-3)

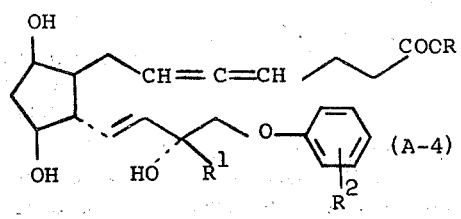

(A-4)

When the compounds of the present invention are racemic mixtures, they are produced starting from racemates, while when the compounds of the invention are individual antimers the compounds are preferably obtained starting from the appropriate individual antimer.

For the sake of simplicity only one antimer, i.e., the antimer having the configuration of natural prostaglandins will be depicted in the description of the process and Claims; however, it is to be understood that the mirror images for the racemic mixtures and the individual antimers are also encompassed thereby.

The use of the symbol "R" preceding a substituent designates the absolute stereochemistry of that substituent according to the Cahn-Ingold-Prelog rules [see Cahn et al., *Angew, Chem. Inter. Edit.*, Vol. 5, p. 385 (1966), errata p. 511; Cahn et al., *Angew. Chem.*, Vol. 78, p. 413 (1966); Cahn and Ingold, *J. Chem. Soc.*, (London), 1951, p. 612; Cahn et al., *Experientia*, Vol. 12, p. 81 (1956); Cahn *J. Chem. Educ.*, Vol. 41, p. 116 (1964)]. Because of the interrelation of the designated substituent with the other substituents in a compound having α or β prefixes, the designation of the absolute configuration of one substituent fixes the absolute configuration of all substituents in the compound and thus the absolute configuration of the compound as a whole.

The term "lower alkyl" as used herein, unless otherwise specified, refers to straight or branched alkyl groups containing up to 4 carbon atoms, e.g., methyl, ethyl, n-propyl, isopropyl, n-butyl, t-butyl and the like.

The term "lower alkoxy" refers to the group $R^1O$- wherein $R^1$ is lower alkyl. Typical lower alkoxy groups include, for example, methoxy, ethoxy, propoxy, isopropoxy, t-butoxy and the like.

The term "pharmaceutically acceptable salts" refers to salts prepared from pharmaceutically acceptable non-toxic bases, including inorganic bases and organic bases. Salts derived from inorganic bases include sodium, potassium, lithium, ammonium, calcium, magnesium, ferrous, zinc, copper, manganous, aluminum, ferric, manganic salts and the like. Particularly preferred are the ammonium, potassium, sodium, calcium and magnesium salts. Salts derived from pharmaceutically acceptable organic non-toxic bases include salts of primary, secondary and tertiary amines, substituted amines including naturally occurring substituted amines, cyclic amines and basic ion exchange resins, such as isopropylamine, trimethylamine, diethylamine, triethylamine, tripropylamine, ethanolamine, 2-dimethylaminoethanol, 2-diethylaminoethanol, tromethamine, lysine, arginine, histidine, caffeine, procaine, hydrabamine, choline, betaine, ethylenediamine, glucosamine, methylglucamine, theobromine, purines, piperazine, piperidine, N-ethylpiperidine, polyamine resins and the like. Particularly preferred organic non-toxic bases are isopropylamine, diethylamine, ethanolamine, piperidine, tromethamine, choline and caffeine.

The novel compounds of the present invention having a secondary hydroxyl group at C-15 (A, $R^1$=H) can be obtained by a process illustrated by the following sequence of reactions:

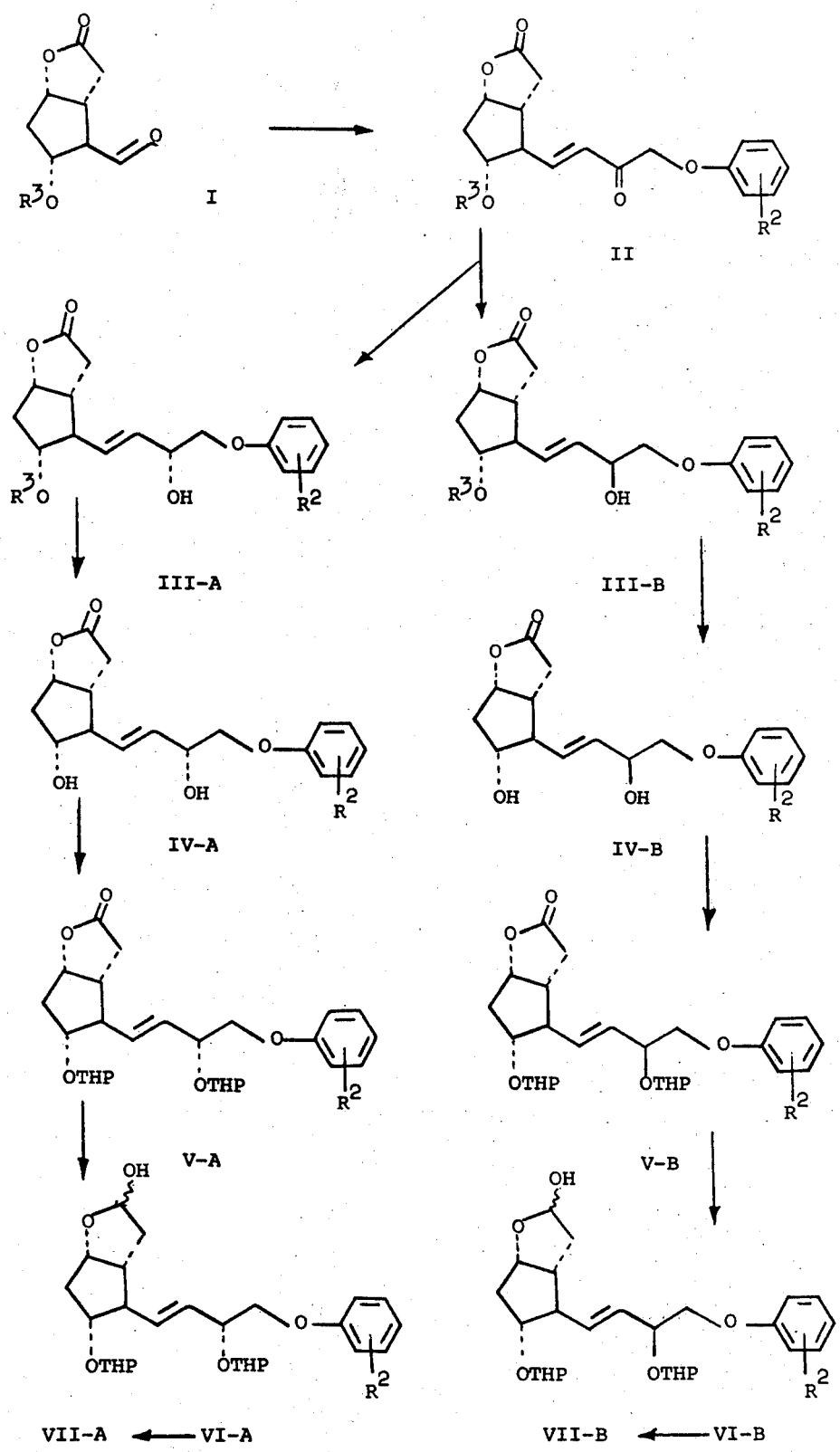

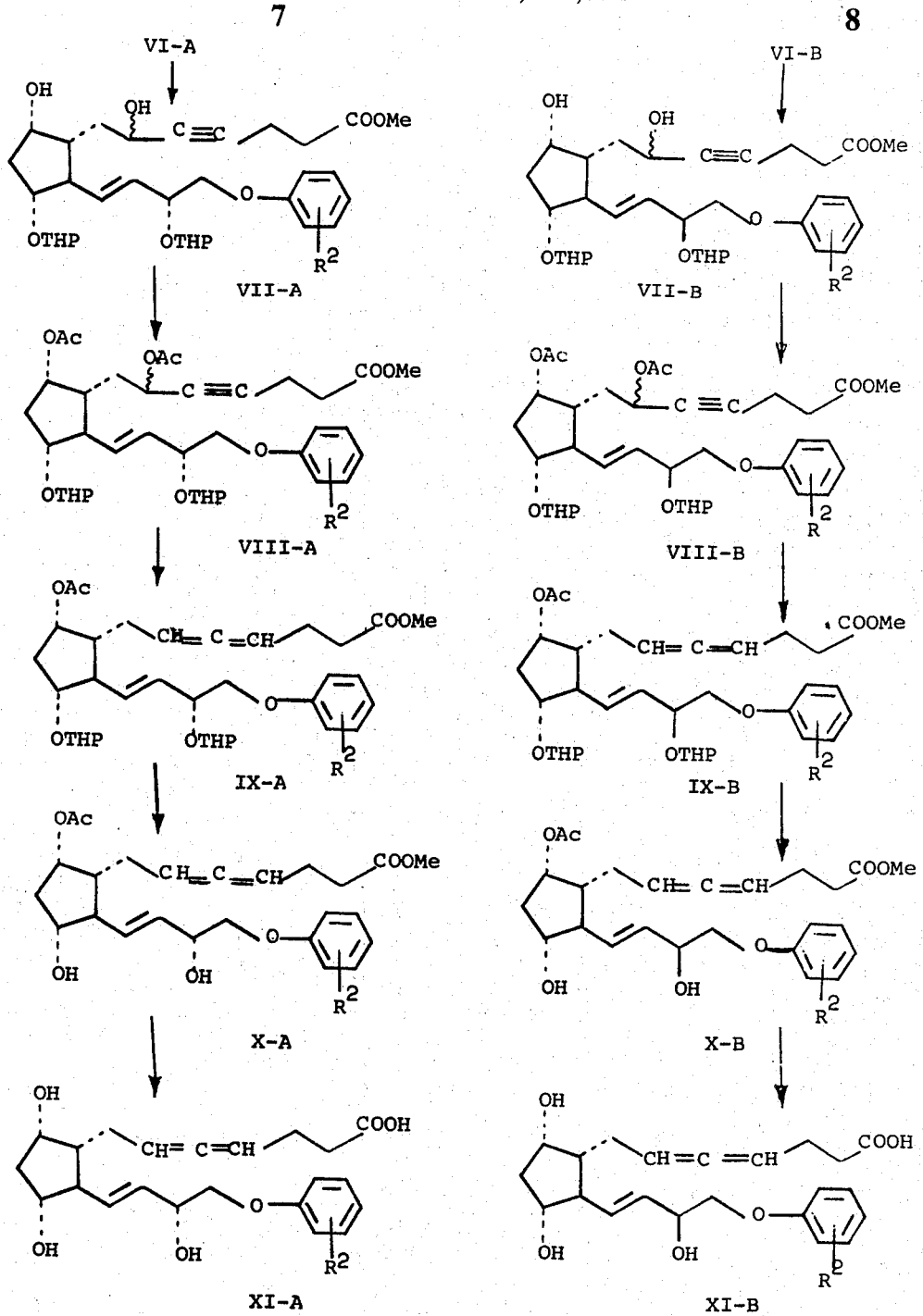

wherein $R^2$ has the above-indicated meaning;

$R^3$ is p-phenylbenzoyl;

Ac is acetyl; and

THP is tetrahydropyranyl.

In practicing the process depicted above, the starting materials of formula I [dl (2'α-hydroxy-4'α-p-phenylbenzoyloxy-5'β-formyl)cyclopent-1'α-yl acetic acid 1,2'-lactone or its 1'R-antimer], are condensed with the sodium anion of a dimethyl 2-oxo-3-phenoxy-(or substituted phenoxy)propylphosphonate of the formula:

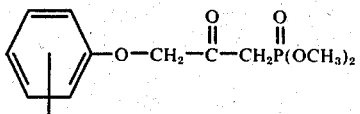

wherein $R^2$ has the above indicated meaning, to yield the corresponding racemic or 1'R-antimeric compound of formula II.

This reaction is conducted in an inert organic solvent, under anhydrous conditions, at a temperature of the order of about 0° C to about 70° C, preferably at about room temperature, for a period of time of about 45 minutes to about 2 hours, preferably for about one and a half hours, under an inert atmosphere, i.e., under argon or nitrogen atmosphere, using at least one molar equivalent of the reagent per mol of the starting aldehyde (I), and preferably 1.2 to 2 moles.

The dimethyl 2-oxo-3phenoxy (or substituted phenoxy) propylphosphonates used as reagents can be conveniently prepared by treatment of phenol or an appropriate o, m or p-substituted phenol with sodium hydride to form the anion, which upon reaction with ethyl bromoacetate affords the corresponding ethyl phenoxyacetate. The latter is condensed with dimethyl α-lithiomethanephosphonate, in accordance with the method described by E. J. Corey et al., in *J. Am. Chem. Soc.* 88, 5654 (1966), to yield the desired reagent.

Alternatively, these reagents can be prepared from commercially available unsubstituted or monosubstituted phenoxyacetic acids, e.g., o, m or p-chlorophenoxyacetic acid, p-fluorophenoxyacetic acid, o, m or p-methylphenoxyacetic acid o, m, or p-methoxyphenoxyacetic acid, p-ethoxyphenoxyacetic acid and the like, which are converted into the corresponding ethyl esters by conventional methods, such as for example by the Fischer's esterification method followed by condensation of the ethyl esters thus obtained with dimethyl α-lithiomethanephosphonate.

The racemic or 1'R-antimeric compounds of formula II are reduced with aluminum isopropoxide in an anhydrous inert hydrocarbon solvent, e.g., toluene, to yield a mixture of the corresponding α and β-hydroxy compounds, which is separated into the individual isomers by thin layer chromatography on silica gel plates, to obtain the individual isomers of formulas III-A and III-B, respectively, in approximately equal amounts, the α-isomer being less polar than the β-isomer.

This reduction is preferably carried out at reflux temperature for a period of time of the order of about 10 to about 90 minutes, preferably for about 55 minutes, under nitrogen or argon atmosphere, using from 1.5 to 5 molar equivalents of aluminum isopropoxide per mol of compound of formula II.

Alternatively, the reduction of the enone of formula II to compounds of formulas III-A and III-B can be effected with an excess of zinc borohydride in dimethoxyethane solution, at room temperature for about 1 hour; however, better results are obtained when using aluminum isopropoxide.

The individual α and β-hydroxy isomers (III-A and III-B) are then submitted separately to conventional saponification of the p-phenylbenzoyloxy group, using preferably anhydrous potassium carbonate in methanol, at room temperature for about 2 to 4 hours, followed by brief acid treatment, at low temperature, i.e., at about 0° to −10° C, to yield the dihydroxy compounds of formulas IV-A and IV-B, respectively (racemic or 1'R-antimeric).

Upon conventional etherification of the latter compounds with dihydropyran in methylene chloride solution in the presence of p-toluenesulfonic acid there are produced the corresponding bistetrahydropyranyloxy derivatives of formulas V-A and V-B, respectively (racemic or 1'R-antimeric), which are reduced with diisobutylaluminum hydride in toluene solution, to produce the corresponding lactols of formulas VI-A and VI-B (racemic or 1'R-antimeric). In the preferred embodiments the reaction is conducted at temperatures in the range of about −78° to about −60° C, under argon or nitrogen atmosphere, for about 10 minutes to about 30 minutes.

The lactols thus obtained are then treated with an excess of the dilithium salt of 4-pentynoic acid, in a suitable inert organic solvent or mixture of solvents, to produce the respective dihydroxyacetylenic acid, which is immediately esterified with diazomethane in diethyl ether solution in a conventional manner, thus obtaining the corresponding dihydroxyacetylenic acid methyl ester of formulas VII-A and VII-B, respectively (racemic or 8R-antimeric).

The dilithium salt of 4-pentynoic acid is used in amounts comprised between about 5 to about 15 molar equivalents per molar equivalent of starting hemiacetal, using preferably about 10 molar equivalents. This reagent is prepared by reaction of an ethereal solution of 4-pentynoic acid with the lithium anion of diisopropylamine (which in turn is formed by treatment of diisopropylamine with methyllithium in an ether-hexamethylphosphoramide mixture) at a temperature of about −78° to about −50° C., under anhydrous conditions and under an inert atmosphere, such as provided by nitrogen or argon, for a period of time of between about 2 to about 4 hours, and thereafter at room temperature for about 2 hours more. The reagent thus prepared is combined with a solution of the hemiacetal of formulas VI-A or VI-B in an ethereal solvent, maintaining the reaction mixture at a temperature between about 10° to about 30° C for a prolonged period of time, i.e., for about 40 to 72 hours, the reaction time depending upon the temperature used. In the preferred embodiments the reaction is conducted at room temperature (about 25° C) for approximately 60 hours.

The product is isolated by dilution with water, acidification with a weak acid such as oxalic acid, extraction with an organic solvent immiscible with water and evaporation of the solvent under reduced pressure, taking care that the temperature does not exceed 20° C. The crude product is conventionally esterified with diazomethane, and thereafter purified by chromatographic techniques, to yield the racemic or 8R-antimeric compounds of formulas VII-A and VII-B, as a mixture of the 6α and 6β-hydroxy isomers.

The racemic or 8R-antimeric compounds of formulas VII-A and VII-B are then acetylated with acetic anhydride in the presence of 4-dimethylaminopyridine, in an inert organic solvent or mixture of inert organic solvents, using particularly a (5:1) mixture of methylene chloride:triethylamine as solvent; the reaction is preferably carried out at room temperature for about 1 hour, to produce the respective racemic or 8R-antimeric diacetates of formulas VIII-A and VIII-B, respectively.

By reaction of the diacetoxyacetylenic compounds of formulas VIII-A and VIII-B with lithium dimethylcopper there are obtained the corresponding allenic compounds of formulas IX-A and IX-B, respectively. The reaction is conducted in an ethereal solvent, under an inert atmosphere at about −78° to about −50° C, for about 3 to about 7 hours, using about 4 to about 6 molar equivalents of the lithium dimethylcopper reagent in diethyl ether. This reagent is prepared as described, for example, by P. Rona et al., in *J. Am. Chem. Soc.* 91, 3289 (1969). When the reaction is substantially complete, as demonstrated by t.l.c. analysis, the product (IX-A or IX-B, racemic or 8R-antimeric) is isolated from the reaction mixture via conventional techniques, such as dilution with ammonium chloride solution, filtration, evaporation of the organic phase and purification of the residue by chromatography.

Upon cleavage of the tetrahydropyranyloxy-groups by mild acid treatment, using particularly 70% aqueous acetic acid, at room temperature for about 12 to about 16 hours there are produced the corresponding 11α,15α- or 11α,15β-dihydroxy compounds of formulas X-A and X-B, respectively, which in turn are saponified under basic conditions using an alkali metal hydroxide or alkali metal carbonate, particularly potassium carbonate in methanol solution to produce respectively the corresponding compounds of formula XI-A (racemic or 8R-antimeric) 9α,11α,15α-trihydroxy-16-phenoxy-(or substituted phenoxy)-17,18,19,20-tetranorprosta-4,5,13-trans-trienoic acids, or the compounds of formula XI-B (racemic or 8R-antimeric) 9α,11α,15β-trihydroxy-16-phenoxy-(or substituted phenoxy)-17,18,19,20-tetranorprosta-4,5,13-trans-trienoic acids. This hydrolysis is preferably conducted at room temperature, for a prolonged period of time, of the order of about 30 to about 48 hours.

The compounds of formula I used as starting materials, namely dl (2'α-hydroxy-4'α-p-phenylbenzoyloxy-5'β-formylcyclopent-1'α-yl) acetic acid 1,2'-lactone and its 1'R-isomer are known compounds which can be prepared as described by E. J. Corey et al., in *J. Am. Chem. Soc.* 93, 1491 and in U.S. Pat. No. 3,873,598.

The novel prostaglandin analogs substituted at C-15 by a methyl or ethyl group and a tertiary hydroxyl group can be prepared by a process illustrated by the following reaction sequence:

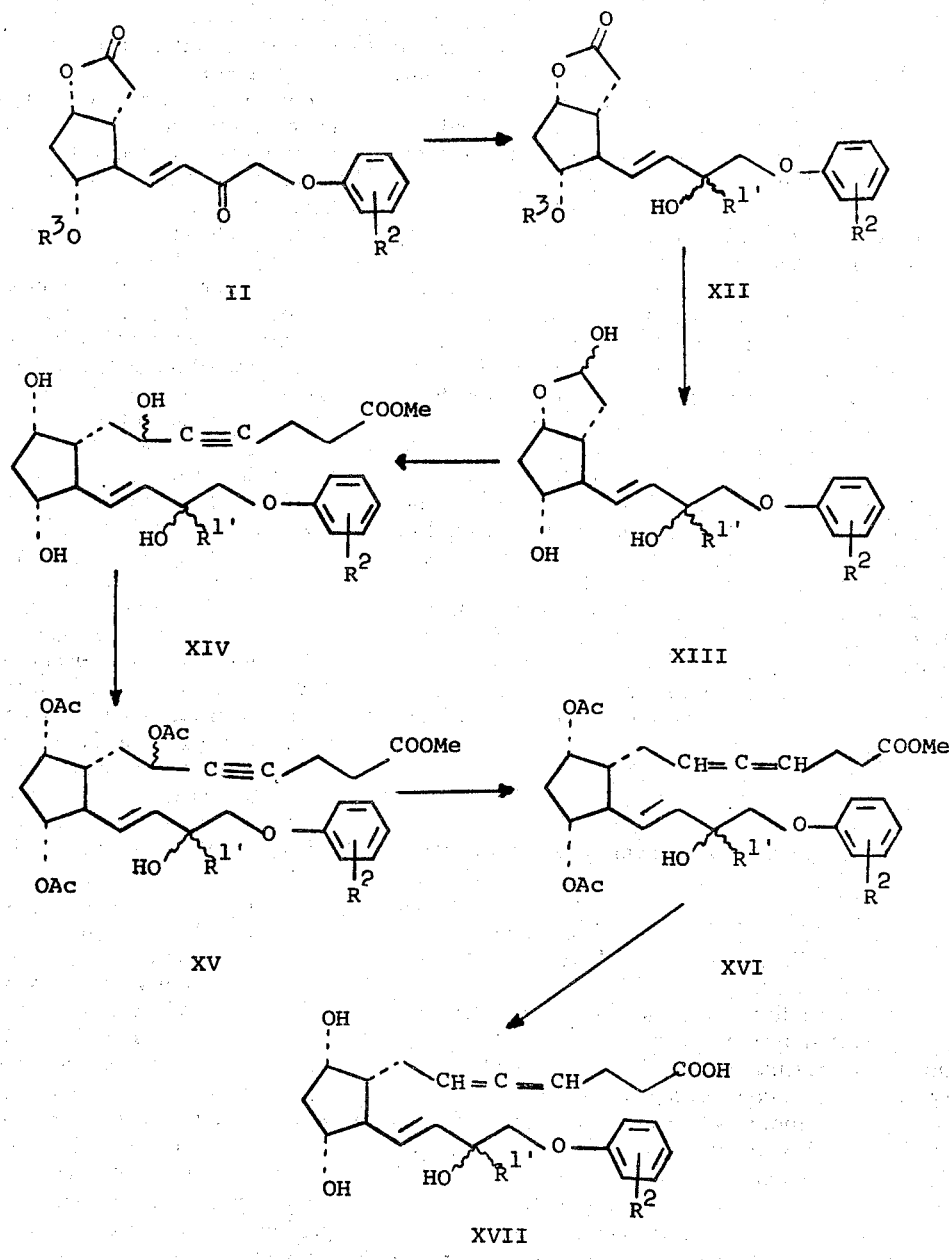

wherein $R^1$ is methyl or ethyl and
$R^2$, $R^3$ and Ac have the above indicated meaning.

In practicing the process depicted above, the starting materials of formula II, i.e., dl {2'α-hydroxy-4'α-p-phenylbenzoyloxy-5'β-[3''-oxo-4''(phenoxy- or substituted phenoxyl)-but-1''(t)-en-1''-yl]cyclopent-1'α-yl} acetic acid 1,2'-lactone or the 1'R-antimeric compound thereof, prepared as described hereinbefore, is treated with a methyl or ethylmagnesium halide to produce the corresponding 15ξ-hydroxy-15 -alkyl derivative of formula XII (mixture of 15α-hydroxy-15β-alkyl and 15β-hydroxy-15α-alkyl isomers). This reaction is preferably carried out in ether or tetrahydrofuran solution under anhydrous conditions and under an inert atmosphere, i.e., under nitrogen or argon atmosphere, using from 1.5 to about 6 molar equivalents of the Grignard reagent, preferably about 4.5 molar equivalents per mol of starting compound, conducting the reaction at a temperature of between −78° to −50° C for about 30 minutes to about 1.5 hours.

Alternatively, the reaction can be effected using methyl- or ethyllithium as reagents.

Treatment of the racemic or 1'R-antimeric compounds of formula XII with diisobutylaluminum hydride in toluene solution produces simultaneously the reduction of the lactone ring and hydrolysis of the p-phenylbenzoyloxy group, thus yielding the corresponding compounds of formula XIII. This reaction is conducted at temperatures in the range of about −78° to about −60° C, under argon or nitrogen atmosphere, for about 10 minutes to about 30 minutes, using from about 6 to about 8 molar equivalents of the reagent per mol of compound XII.

The lactols thus obtained are then treated with an excess of the dilithium salt of 4-pentynoic acid, prepared as described hereinbefore, to produce the corresponding tetrahydroxyacetylenic acid compound, which is immediately esterified with diazomethane in methylene chloride solution, in a conventional manner, to yield the corresponding methyl ester derivative of formula XIV.

The reaction conditions for the introduction of the acetylenic side chain are essentially the same as those previously described for the transformation of compounds VI-A and VI-B into VII-A and VII-B. However, best results are obtained when the reaction is conducted in a dilute solution, preferably increasing the amount of hexamethylphosphoramide up to 5 fold the amount used in the case of compounds VI-A and VI-B once the reagent and starting lactol of formula XIII are combined. The reaction is preferably conducted at room temperature, for a period of time ranging between about 20 hours to about 60 hours.

Conventional esterification of the racemic or 8R-antimeric compounds of formula XIV with acetic anhydride in pyridine solution, preferably at room temperature for about 3 to about 4 hours produces the respective racemic or 8R-antimeric triacetates of formula XV.

By treatment of the racemic or 8R-antimeric triacetoxyacetylenic compounds of formula XV with lithium dimethylcopper in diethyl ether solution there are obtained the corresponding allenic compounds of formula XVI. The reaction is conducted under an inert atmosphere, at about −78° to about −50° C, for about 3 to about 7 hours, using about 4 to about 6 molar equivalents of the reagent per mol of acetylenic starting compound.

The methyl ester and acetyl protecting groups are then eliminated by alkaline treatment, i.e., treatment with an alkali metal hydroxide or alkali metal carbonate such as sodium hydroxide, potassium hydroxide, sodium carbonate, potassium carbonate and the like, in a lower aqueous aliphatic alcohol, using particularly potassium carbonate in aqueous methanol, to produce the corresponding racemic or 8R antimeric free acids of formula XVII. This hydrolysis reaction is preferably conducted at room temperature, for a prolonged period of time of the order of about 80 hours to about 120 hours. For the isolation of the product from the reaction mixture it is convenient to work it up under slightly acidic conditions, i.e., at a pH of about 6, by using a buffered solution of citric acid-disodium hydrogen phosphate, thus avoiding dehydration of the prostaglandin product. After removal of the neutral materials, the free acid is isolated from the aqueous buffered solution by repeated extractions with a solvent immiscible with water, e.g., ethyl acetate, methylene chloride, diethyl ether and the like, and purified by thin layer chromatography, to obtain a mixture of the 15α-hydroxy-15β-methyl(ethyl)- and 15β-hydroxy-15α-methyl(ethyl)prostatrienoic acids (XVII).

The compounds of formulas XI-A, XI-B and XVII can be converted into the corresponding alkyl esters by methods known in the art, i.e., by treatment of the free acid with an excess of a diazoalkane, such as diazomethane, diazoethane or diazopropane in ether or methylene chloride solution, in a conventional manner, or by reaction with the desired lower alkyl iodide in the presence of lithium carbonate, at room temperature.

The salt derivatives of the prostatrienoic acids of the present invention can be prepared by treating the corresponding free acids with about one molar equivalent of a pharmaceutically acceptable base, including inorganic and organic bases per molar equivalent of free acid. Salts derived from inorganic bases include sodium, potassium, lithium, ammonium, calcium, magnesium, ferrous, zinc, copper, manganous, aluminum, ferric, manganic salts and the like. Particularly preferred are the ammonium, potassium, sodium, calcium and magnesium salts. Salts derived from pharmaceutically acceptable organic non-toxic bases include salts of primary, secondary and tertiary amines, substituted amines including naturally occurring substituted amines, cyclic amines and basic ion exchange resins, such as isopropylamine, trimethylamine, diethylamine, triethylamine, tripropylamine, ethanolamine, 2-dimethylaminoethanol, 2-diethylaminoethanol, tromethamine, lysine, arginine, histidine, caffeine, procaine, hydrabamine, choline, betaine, ethylenediamine, glucosamine, methylglucamine, theobromine, purines, piperazine, piperidine, N-ethylpiperidine, polyamine resins and the like. Particularly preferred organic non-toxic bases are isopropylamine, diethylamine, ethanolamine, piperidine, tromethamine, choline and caffeine.

The reaction is conducted in water, alone or in combination with an inert, water-miscible organic solvent, at a temperature of from about 0° to about 100° C., preferably at room temperature. Typical inert, water-miscible organic solvents include methanol, ethanol, isopropanol, butanol, acetone, dioxane or tetrahydrofuran. The molar ratio of the free acid (XI-A, XI-B and XVII) to base used are chosen to provide the ratio desired for any particular salt. For preparing, for example, the calcium salts or magnesium salts, the free acid starting material can be treated with at least 0.5 molar equivalent of pharmaceutically acceptable base to yield a neutral salt. When the aluminum salts are prepared, at least one third molar equivalent of the pharmaceutically acceptable base are employed if a neutral salt product is desired.

In the preferred procedure, the calcium salts and magnesium salts of the prostatrienoic acid compounds hereof can be prepared by treating the corresponding sodium or potassium salts with at least 0.5 molar equivalent of calcium chloride or magnesium chloride, respectively, in an aqueous solution, alone or in combination with an inert water miscible organic solvent, at a temperature of from about 20° to about 100° C. Preferably, the aluminum salts of the prostanoic acids of the present invention can be prepared by treating the corresponding free acids with at least one third molar equivalent of an aluminum alkoxide, such as aluminum triethoxide, aluminum tripropoxide and the like, in a hydrocarbon solvent, such as benzene, xylene, cyclohexane and the like, at a temperature of from 20° to about 115° C. Similar procedures can be used to prepare salts of inorganic bases which are not sufficiently soluble for easy reaction.

The salt products are isolated by conventional methods.

The compounds of the present invention exhibit prostaglandin-like biological activities and thus are useful in the treatment of mammals where the use of prostaglandins is indicated.

Particularly, these compounds have luteolytic activity and thus are useful for controlling the reproductive cycle in female mammals and for inducing estrus and regulating ovulation in female animals such as horse, cow and swine. They are also useful for inducing labor in pregnancy and for inducing menses in human females, to correct or reduce menstrual abnormalities.

The compounds of the present invention are also bronchodilators and thus are useful in treating mammals for bronchial spasm or wherever bronchodilators are indicated. They are also useful in controlling or palliating hypertension in mammals and further exhibit central nervous system depressant activity in mammals, and are useful as sedatives.

The present compounds can be administered in a wide variety of dosage forms, either alone or in combination with other pharmaceutically compatible medicaments, in the form of pharmaceutical compositions suited for oral or parenteral administration or inhalation in the case of bronchodilators. Intravaginal and intrauterine are alternative routes of administration. They are typically administered as pharmaceutical compositions consisting essentially of the free acid, salt or ester of the invention and a pharmaceutical carrier. The pharmaceutical carrier can be either a solid material, liquid or aerosol, in which the compound (free acid, salt or ester) is dissolved, dispersed or suspended, and can optionally contain small amounts of preservatives and/or pH buffering agents. Suitable preservatives which can be used include, for example, benzyl alcohol and the like. Suitable buffering agents include, for example, sodium acetate and pharmaceutical phosphate salts and the like.

The liquid compositions can, for example, be in the form of solutions, emulsions, suspensions, syrups, or elixirs. The solid compositions can take the form of tablets, powders, capsules, pills or the like, preferably in unit dosage forms for simple administration or precise dosages. Suitable solid carriers include, for example, pharmaceutical grades of starch, lactose, sodium saccharin, talcum, sodium bisulfite and the like.

For inhalation administration, the free acids, salts and esters can, for example, be administered as an aerosol comprising the compounds or salts in an inert propelant together with a cosolvent e.g., ethanol, together with optional preservatives and buffering agents. Additional general information concerning the inhalation administration of aerosols can be had by reference to U.S. Pat. Nos. 2,868,691 and 3,095,355.

The compounds of this invention are typically administered in dosages of about from 0.002 to 0.2 mg. per Kg. of body weight. The precise effective dosage will, of course, vary depending upon the mode of administration, condition being treated and host.

The followng examples illustrate the invention, but are not intended to limit its scope. When racemic mixtures are used as starting materials, there are obtained racemic products, while when using individual antimers, the products obtained are antimeric. The abbreviation t.l.c. refers to thin-layer chromatography and all mixture ratios used with regard to liquids refer to volume ratios. Also, where necessary, examples are repeated to provide sufficient starting material for subsequent examples.

EXAMPLE 1

A. A 57% suspension of 5.32 g. (126.5 mmoles) of sodium hydride in mineral oil is washed three times with anhydrous hexane, under argon atmosphere, 500 ml. of anhydrous dimethoxyethane is added, the mixture is cooled in an ice-water bath and treated dropwise with stirring, in a 5 minute period, with a solution of 18.43 g. (113.7 mmoles) of m-trifluoromethylphenol in 100 ml. of anhydrous dimethoxyethane. When the addition is complete the reaction mixture is allowed to attain room temperature and stirred for 40 additional minutes. A solution of 19.572 g. (117 mmoles) of ethyl bromoacetate in 100 ml. of anhydrous dimethoxyethane is then added and the resulting mixture is refluxed for 1 hour, cooled to room temperature, neutralized with acetic acid and evaporated to dryness under reduced pressure. The residue is taken up in 600 ml. of methylene chloride and 70 ml. of water, the organic phase is separated and washed with water (4 × 70 ml.), dried over anhydrous magnesium sulfate and evaporated to dryness under vacuum, to yield 28.81 g. of ethyl m-trifluoromethylphenoxyacetate, b.p. 122°–123° C/13.5 mm.

B. A stirred mixture of 15.12 g. (121.97 mmoles) of dimethyl methylphosphonate and 200 ml. of anhydrous tetrahydrofuran is cooled to −78° C under an atmosphere of argon and treated dropwise in a 15 minute period, with 57.35 ml. of a 2.125N solution of n-butyllithium, (121.97 mmoles) in hexane, maintaining the temperature of the reaction mixture at a temperature not higher than −65° C. The resulting mixture is stirred for 15 minutes further at −78° C and then a solution of 28.81 g. (116.16 mmoles) of ethyl m-trifluoromethylphenoxyacetate in 300 ml. of anhydrous tetrahydrofuran is added dropwise, in a 25 minute period, maintaining the temperature of the reaction mixture at a temperature not higher than −65° C, the resulting mixture is then stirred for 2 hours further at room temperature, neutralized with acetic acid and the solvent eliminated under vacuum. The residue is taken up in diethyl ether-water (1:1), the organic phase is separated and the aqueous phase extracted with diethyl ether (3 × 200 ml.). The combined organic extracts are washed with water, dried over anhydrous magnesium sulfate and evaporated to dryness under reduced pressure, to yield 35.78 g. of dimethyl 2-oxo-3-(m-trifluoromethylphenoxy) propylphosphonate.

C. A 57% suspension of 42 mg. (1 mmol) of sodium hydride in mineral oil is washed with anhydrous hexane, under argon atmosphere, 3 ml. of anhydrous dimethoxyethane is then added, and thereafter, a solution of 358.6 mg. (1.1 mmoles) of dimethyl 2-oxo-3-(m-trifluoromethylphenoxy)propylphosphonate in 10 ml. of anhydrous dimethoxyethane, stirring the resulting mixture at room temperature for 30 minutes. To the solution thus obtained there is added a solution of 0.8 mmoles of dl (2′α-hydroxy-4′α-p-phenylbenzoyloxy-5′β-formylcyclopent-1′α-yl)acetic acid 1,2′-lactone in 10 ml. of anhydrous dimethoxyethane. The reaction mixture is stirred at room temperature for 1 hour and 10 minutes, 0.07 ml. of acetic acid are then added and the solvent is eliminated under reduced pressure. The residue is extracted with methylene chloride and the combined extracts washed with saturated sodium chloride solution, dried over anhydrous magnesium sulfate and evaporated to dryness under vacuum. The oily residue is purified by t.l.c. using a methylene chloride-ether mixture (1:3) as eluant to yield 215 mg. of dl {2′α-hydroxy-4′α-p-phenylbenzoyloxy-5′β-[3′′-oxo-4′′-(m-trifluoromethylphenoxy)-but-1′′(t)-en-1′′-yl]cyclopent-1′α-yl} acetic acid 1,2′-lactone, (racemic II, $R^2$ = m-CF$_3$), m.p. 126°–126.5° C.

In a similar manner, but using 1′R-(2′α-hydroxy-4′α-p-phenylbenzoyloxy-5′β-formylcyclopent-1′α-yl) acetic acid 1,2′-lactone in place of the racemic compound, there is obtained 1′R-{2′α-hydroxy-4′α-p-phenylbenzoyloxy-5′β-[3′′-oxo-4′′-(m-trifluoromethylphenoxy)-but-1′′(t)-en-1′′-yl] cyclopent-1′α-yl} acetic acid 1,2′-lactone (1′R-antimer of II, $R^2$ = m-CF$_3$).

EXAMPLE 2

A mixture of 100 mg. (0.182 mmoles) of dl { 2′α-hydroxy-4′α-p-phenylbenzoyloxy-5′β-[3′′-oxo-4′′-(m-trifluoromethylphenoxy)-but-1′′(t)-en-1′′-yl]cyclopent-1′α-yl} acetic acid 1,2′-lactone, 62 mg. (0.303 mmoles) of redistilled aluminum isopropoxide and 5 ml. of anhydrous toluene is refluxed under argon atmosphere and with stirring for 55 minutes; it is then cooled, a solution of sodium bitartrate is added and the product extracted with ethyl acetate. The organic extract is washed with water, dried over magnesium sulfate and evaporated to dryness under reduced pressure. The residue is purified by t.l.c. using a diethyl ether:benzene:methylene chloride mixture (2:1:1) as eluant to obtain 36.4 mg of dl {2′α-hydroxy-4′α-p-phenylbenzoyloxy-5′β-[3′′α-hydroxy-4′′-(m-trifluoromethylphenoxy)-but-1′′(t)-en-1′′-yl]cyclopent-1′α-yl} acetic acid 1,2′-lactone (racemic III-A, $R^2$ = m-CF$_3$) as an oil, having the following constants:
U.V. $\lambda_{max}^{MeOH}$ 274 nm (log ε 4.387) (ε 24,350);
I.R. $\nu_{max}^{CHCl_3}$ 3600, 1775, 1715, 1610 cm$^{-1}$;
N.M.R. $\delta_{TMS}^{CDCl_3}$ 2.22–2.97 (m, 6H, H-2,1′,3′,5′);
 3.80–4.07 (m, 2H, H-4′′);
 4.32–4.67 (m, 1H, H-3′′);
 4.87–5.40 (m, 2H, H-2′,4′);
 5.67–5.90 (m, 2H, H-1′′,2′′);
 6.97–7.12 (m, 13H, aromatic);
and 38 mg. of dl {2′α-hydroxy-4′α-p-phenylbenzoyloxy-5′β-[3′′β-hydroxy-4′′-(m-trifluoromethylphenoxy)-but-1′′(t)-en-1′′-yl] cyclopent-1′α-yl} acetic acid 1,2′-lactone (racemic III-B, $R^2$ = m-CF$_3$), also an oil, having the following constants:

U.V. $\lambda_{max}^{MeOH}$ 274 nm (log ε 4.426) (ε26,650);
I.R. $\nu_{max}^{CHCl_3}$ 3600, 1775, 1715, 1610 cm$^{-1}$;
N.M.R. $\Gamma_{TMS}^{CDCl_3}$ 2.20–2.90 (m, 6H, H-2,1′,3′,5′);
 3.73–4.07 (m, 2H, H-4′′);
 4.32–4.67 (m, 1H, H-3′′);
 4.87–5.40 (m, 2H, H-2′,4′);
 5.67–5.83 (m, 2H, H-1′′,2′′);
 6.93–7.10 (m, 13H, aromatic).

In a similar manner, starting from 1′R-{2′α-hydroxy-4′α-p-phenylbenzoyloxy-5′β-[3′′-oxo-4′′-(m-trifluoromethylphenoxy)-but-1′′(t)-en-1′′-yl]cyclopent-1′β-yl} acetic acid 1,2′-lactone there are obtained 1′R-{2′α-hydroxy-4′α-p-phenylbenzoyloxy-5′β-[3′′α-hydroxy-4′′-(m-trifluoromethylphenoxy)-but-1′′(t)-en-1′′-yl]cyclopent-1′α-yl} acetic acid 1,2′-lactone (1′-R-antimer of III-A, $R^2$ = m-CF$_3$) and 1′R-{2′α-hydroxy-4′α-p-phenylbenzoyloxy-5′β-[3′′β-hydroxy-4′′-(m-trifluoromethylphenoxy)-but-1′′(t)-en-1′′-yl] cyclopent-1′α-yl} acetic acid 1,2′-lactone (1′R-antimer of III-B, $R^2$ = m-CF$_3$).

EXAMPLE 3

To a stirred solution of 390 mg. (0.706 mmoles) of dl {2′α-hydroxy-4′α-p-phenylbenzoyloxy-5′β-[3′′α-hydroxy-4′′-(m-trifluoromethylphenoxy)-but-1′′(t)-en-1′′-yl]cyclopent-1′α-yl} acetic acid 1,2′-lactone in 4 ml. of anhydrous methanol is added 97.5 mg. (0.706 mmoles) of anhydrous potassium carbonate, and the resulting mixture is stirred at room temperature for 2½ hours. It is then cooled to −10° C and 0.9 ml. of concentrated hydrochloric acid are added, the resulting mixture is kept at this temperature for 10 minutes, diluted with cold ethyl acetate and washed with saturated sodium potassium tartrate solution (3 × 30 ml.), dried over anhydrous magnesium sulfate and evaporated to dryness under reduced pressure. The residue is purified by t.l.c. using ethyl acetate:methylene chloride (9:1) as eluant, to obtain 180 mg. of dl {2′α,4′α-dihydroxy-5′β-[3′′α-hydroxy-4′′-(m-trifluoromethylphenoxy)-but-1′′(t)-en-1′′-yl]cyclopent-1′α-yl} acetic acid 1,2′-lactone (racemic IV-A, $R^2$ = m-CF$_3$), as an oil, having the following constants:
U.V. $\lambda_{max}^{MeOH}$ 222, 275, 282 nm (log ε 3.93, 3.36, 3.31); (ε 8500, 2290, 2040);
I.R. $\nu_{max}^{CHCl_3}$ 3610, 3440, 1770, 1595 cm$^{-1}$;
N.M.R. $\delta_{TMS}^{CDCl_3}$ 2.20–2.70 (m, 6H, H-2,1′,3′,5′);
 3.73–4.13 (m, 3H, H-4′′,4′);
 4.27–4.63 (m, 1H, H-3′′);
 4.63–5.00 (m, 1H, H-2′);
 5.50–5.77 (m, 2H, H-1′′,2′′);
 7.00–7.33 (m, 4H, aromatic).

EXAMPLE 4

To a stirred solution of 2.25 g. (4.075 mmoles) of dl{2′α-hydroxy-4′α-p-phenylbenzoyloxy-5′β-[3′′β-hydroxy-4′′-(m-trifluoromethylphenoxy)-but-1′′(t)-en-1′′-yl] cyclopent-1′α-yl} acetic acid 1,2′-lactone in 18.3 ml. of anhydrous methanol is added 678 mg. (4.90 mmoles) of anhydrous potassium carbonate, and the resulting mixture is stirred at room temperature for 2 hours and 45 minutes. The reaction mixture is then cooled to −10° C and 8.15 ml. of concentrated hydrochloric acid are added, the resulting mixture is stirred at this temperature for 10 minutes, diluted with ethyl acetate, the organic layer is separated and washed with saturated sodium potassium tartrate solution (3 × 25 ml.), dried over anhydrous magnesium sulfate and evaporated to dryness under reduced pressure. The residue is dissolved in a 1:1 mixture of ethyl acetate:-methylene chloride and passed through a column of Florisil (75 g.). The eluates are evaporated to dryness under vacuum and purified by t.l.c., using ethyl acetate:methylene chloride (8:2) as eluant, to obtain 1.35 g. of dl {2'α,4'α-dihydroxy-5'β-[3''β-hydroxy-4''-(m-trifluoromethylphenoxy)-but-1'''(t)-en-1'''-yl]cyclopent-1'α-yl} acetic acid 1,2'-lactone (racemic IV-B, $R^2$ = m-CF$_3$), as an oil, which has the following constants:

U.V. $\lambda_{max}^{MeOH}$ 222, 275, 282 nm (log ε 3.93, 3.32, 3.29) (ε 2470, 2090, 1950);
I.R. $\nu_{max}^{CHCl_3}$ 3610, 3450, 2390, 1775, 1595 cm$^{-1}$;
N.M.R. $\delta_{TMS}^{CDCl_3}$ 2.20–2.75 (m, 6H, H-2,1',3',5');
  3.70–4.13 (m, 3H, H-4'',4');
  4.27–4.63 (m, 1H, H-3'');
  4.63–5.00 (m, 1H, H-2');
  5.50–5.77 (m, 2H, H-1''',2''');
  7.00–7.33 (m, 4H, aromatic).

Likewise, starting from 1'R-{2'α-hydroxy-4'α-p-phenylbenzoyloxy-5'β-[3''α-hydroxy-4''-(m-trifluoromethylphenoxy)-but-1'''(t)-en-1'''-yl]cyclopent-1'α-yl} acetic acid, 1,2'-lactone and 1'R-{2'α-hydroxy-4'α-p-phenylbenzoyloxy-5'β-[3''β-hydroxy-4''-(m-trifluoromethylphenoxy)-but-1'''(t)-en-1'''-yl] cyclopent-1'α-yl} acetic acid 1,2'-lactone there are obtained, respectively: 1'R-{2'α,4'α-dihydroxy-5'β-[3''α-hydroxy-4''-(m-trifluoromethylphenoxy)-but-1'''(t)-en-1'''-yl]cyclopent-1'α-yl} acetic acid 1,2'-lactone (1'R-antimer of IV-A, $R^2$ = m-CF$_3$) and 1'R-{2'α,4'α-dihydroxy-5'β-[3''β-hydroxy-4''-(m-trifluoromethylphenoxy)-but-1'''(t)-en-1'''-yl]cyclopent-1'α-yl} acetic acid 1,2'-lactone (1'R-antimer of IV-B, $R^2$ = m-CF$_3$).

EXAMPLE 5

To a solution of 1.243 g. of dl{2'α,4'α-dihydroxy-5'β-[3''α-hydroxy-4''-(m-trifluoromethylphenoxy)-but-1'''(t)-en-1'''-yl]cyclopent-1'α-yl} acetic acid 1,2'-lactone in 8.9 ml. of anhydrous methylene chloride there are added 9 mg. of p-toluenesulfonic acid and 0.89 ml. of freshly distilled dihydropyran, and the resulting mixture is stirred at room temperature for 15 minutes, 0.33 ml. of pyridine are then added, the mixture is diluted with ether and washed with sodium chloride solution (3 × 25 ml.), the ethereal solution is dried over anhydrous magnesium sulfate and evaporated to dryness under reduced pressure. Purification of the residue by t.l.c. using ethyl acetate:methylene chloride (2:8) affords 1.75 g. of dl {2'α-hydroxy-4'α-tetrahydropyranyloxy-5'β-[3''α-tetrahydropyranyloxy-4''-(m-trifluoromethylphenoxy)-but-1'''(t)-en-1'''-yl]cyclopent-1'α-yl} acetic acid 1,2'-lactone (racemic V-A, $R^2$ = m-CF$_3$) as an oil, having an
I.R. $\nu_{max}^{CHCl_3}$ 1775, 1595 cm$^{-1}$.

In a similar manner, starting from dl {2'α,4'α-dihydroxy-5'β-[3''β-hydroxy-4''-(m-trifluoromethylphenoxy)-but-1'''(t)-en-1'''-yl]cyclopent-1'α-yl} acetic acid 1,2'-lactone there is obtained dl {2'α-hydroxy-4'α-tetrahydropyranyloxy-5'β-[3''β-tetrahydropyranyloxy-4''-(m-trifluoromethylphenoxy)-but-1'''(t)-en-1'''-yl]cyclopent-1'α-yl} acetic acid 1,2'-lactone (racemic V-B, $R^2$ = m-CF$_3$), as an oil, which has the following constants:

U.V. $\lambda_{max}^{MeOH}$ 221.5, 274.5, 281 nm (log ε 4.03, 3.94, 3.43) (ε 10,700, 8700, 2690);
I.R. $\nu_{max}^{CHCl_3}$ 1775, 1595 cm$^{-1}$;
N.M.R. $\delta_{TMS}^{CDCl_3}$ 1.20–1.97 (m, 12H, H-THP);
  2.00–2.38 (m, 4H, H-2,1',5');
  3.20–4.20 (m, 8H, H-3',4''', THP);
  4.28–5.20 (m, 5H, H-2',4', THP);
  5.40–5.88 (m, 2H, H-1''',2''');
  6.93–7.20 (m, 4H, aromatic).

By the same method, 1'R- {2'α,4'α-dihydroxy-5'β-[3''α-hydroxy-4''-(m-trifluoromethylphenoxy)-but-1'''(t)-en-1'''-yl]cyclopent-1'α-yl} acetic acid 1,2'-lactone and 1'R-{2'α,4'α-dihydroxy-5'β-[3''β-hydroxy-4''-(m-trifluoromethylphenoxy)-but-1'''(t)-en-1'''-yl]cyclopent-1'α-yl} acetic acid 1,2'-lactone are converted respectively into 1'R- {2'α-hydroxy-4'α-tetrahydropyranyloxy-5'β-[3''α-tetrahydropyranyloxy-4''-(m-trifluoromethylphenoxy)-but-1'''(t)-en-1'''-yl]cyclopent-1'α-yl} acetic acid 1,2'-lactone (1'R-antimer of V-A, $R^2$ = m-CF$_3$) and 1'R-{2'α-hydroxy-4'α-tetrahydropyranyloxy-5'β-[3''β-tetrahydropyranyloxy-4''-(m-trifluoromethylphenoxy)-but-1'''(t)-en-1'''-yl]cyclopent-1'α-yl} acetic acid 1,2'-lactone (1'R-antimer of V-B, $R^2$ = m-CF$_3$).

EXAMPLE 6

A solution of 1.750 g. (3.24 mmoles) of dl {2'α-hydroxy-4'α-tetrahydropyranyloxy-5'β-[3''α-tetrahydropyranyloxy-4''-(m-trifluoromethylphenoxy)-but-1'''(t)-en-1'''-yl]cyclopent-1'α-yl} acetic acid 1,2'-lactone in 30 ml. of anhydrous toluene is cooled to −78° C and treated dropwise, under stirring and under argon atmosphere with 5.55 ml. (7.78 mmoles) of diisobutylaluminum hydride-toluene (1:3). The reaction mixture is stirred under the same conditions for 15 minutes further and methanol is carefully added until the evolution of gas ceases; it is then diluted with ether, 5-ml. of saturated sodium chloride solution are then added and the resulting mixture is stirred until a precipitate is formed. The solid material is separated by filtration through Celite (diatomaceous earth). The organic layer is separated from the filtrate, dried over magnesium sulfate and evaporated to dryness under vacuum, thus obtaining 1.65 g. of dl {2'α-hydroxy-4'α-tetrahydropyranyloxy-5'β-[3''α-tetrahydropyranyloxy-4''-(m-trifluoromethylphenoxy)-but-1'''(t)-en-1'''-yl]cyclopent-1'α-yl} acetaldehyde 1,2'-hemiacetal (racemic VI-A, $R^2$ = m-CF$_3$), as an oil, which has the following constants:

U.V. $\lambda_{max}^{MeOH}$ 222, 275, 280–284 nm (log ε 3.92, 3.31, 3.27) (ε 8300, 2040, 1860);
I.R. $\nu_{max}^{CHCl_3}$ 3620, 3410, 1595 cm$^{-1}$;
N.M.R. $\delta_{TMS}^{CDCl_3}$ 1.10–2.6 (m, 16H, H-2,1',3',5', THP);
  3.20–4.17 (m, 6H, H-4''', THP);
  4.20–4.97 (m, 5H, H-2',4',3'', THP);
  5.20–5.80 (m, 3H, H-1,1''',2''');
  6.90–7.32 (m, 4H, aromatic).

Likewise, starting from 1'R- {2'α-hydroxy-4'α-tetrahydropyranyloxy-5'β-[3''α-tetrahydropyranyloxy-4''-(m-trifluoromethylphenoxy)-but-1'''(t)-en-1'''-yl]cyclopent-1'α-yl} acetic acid 1,2'-lactone there is obtained 1'R {2'α-hydroxy-4'α-tetrahydropyranyloxy-5'β-[3''α-tetrahydropyranyloxy-4''-(m-trifluoromethylphenoxy)-but-1'''(t)-en-1'''-yl]cyclopent-1'α-yl} acetaldehyde 1,2'-hemiacetal (1'R-antimer of VI-A, $R^2$ = m-CF$_3$).

EXAMPLE 7

A solution of 1.92 g. (3.57 mmoles) of dl {2'α-hydroxy-4'α-tetrahydropyranyloxy-5'β-[3''β-tetrahydropyranyloxy-4''-(m-trifluoromethylphenoxy)-but-1'''(t)-en-1'''-yl]cyclopent-1'α-yl} acetic acid 1,2'-lactone in 32 ml. of anhydrous toluene is cooled to −78° C and treated dropwise, with stirring and under argon atmosphere with 5.98 ml. (8.4 mmoles) of diisobutylaluminum hydride-toluene (1:3). The reaction mixture is maintained under the same conditions for 15 minutes further and treated dropwise with methanol until the evolution of gas ceases. It is then diluted with 100 ml. of ether, 5 ml. of saturated sodium chloride solution are then added and the resulting mixture is stirred until a precipitate is formed. The solid material is separated by filtration through Celite (diatomaceous earth). The organic layer is separated from the filtrate, dried over magnesium sulfate and evaporated to dryness under vacuum, thus obtaining 1.855 g. of dl {2'α-hydroxy-4'α-tetrahydropyranyloxy-5'β-[3''β-tetrahydropyranyloxy-4''-(m-trifluoromethylphenoxy)-but-1'''(t)-en-1'''-yl]cyclopent-1'α-yl} acetaldehyde 1,2'-hemiacetal (racemic VI-B, $R^2$ = m-$CF_3$), an oil, having the following constants:

U.V. $\lambda_{max}^{MeOH}$ 222, 275, 280–284 nm (log ϵ3.93, 3.32, 3.27) (ϵ2470, 2090, 1860);
I.R. $\nu_{max}^{CHCl_3}$ 3610, 3410, 1595 cm$^{-1}$;
N.M.R. $\delta_{TMS}^{CDCl_3}$ 1.10–2.60 (m, 16H, H-2,1',3',5', THP);
3.20–4.97 (m, 6H, H-4'', THP); 4.20–4.97 (m, 5H, H-2',4'3'', THP; 5.20–5.80 (m, 3H, H-1,1'',2'');
6.90–7.32 (m, 4H, aromatic).

In a similar manner, 1'R-{2'α-hydroxy-4'α-tetrahydropyranyloxy-5'β-[3''β-tetrahydropyranyloxy-4''-(m-trifluoromethylphenoxy)-but-1'''-(t)-en-1'''-yl]cyclopent-1'α-yl} acetic acid 1,2'-lactone is converted into 1'R-{2'α-hydroxy-4'α-tetrahydropyranyloxy-5'β-[3''β-tetrahydropyranyloxy-4''-(m-trifluoromethylphenoxy)-but-1-'''(t)-en-1'''-yl]cyclopent-1'α-yl} acetaldehyde 1,2'-hemiacetal (1'R-antimer of VI-B, $R^2$ = m-$CF_3$).

EXAMPLE 8

A mixture of 50 ml. of anhydrous ether, 5.83ml (42.2 mmoles) of diisopropylamine (distilled over methylmagnesium bromide) and 6.97 g. (43 mmoles) of hexamethylphosphoramide (distilled from sodium hydride) is cooled to −10° C under argon atmopshere and to the cold mixture is added dropwise 22.7 ml. of a 1.9M solution of methyllithium in ether (42.3 mmoles). The reaction mixture is stirred for 10 minutes under the same conditions, it is then cooled to −78° C and treated with a solution of 2.135 g. (21.75 mmoles of 4-pentynoic acid in 50 ml. of anhydrous ether (a precipitate is formed during the addition). When the addition is complete the temperature of the reaction mixture is allowed to attain room temperature and maintained for 2 hours further. A solution of 1.615 g. (2.97 mmoles) of dl {2'α-hydroxy-4'α-tetrahydropyranyloxy-5'β-[3'λ'α-tetrahydropyranyloxy-4''-(m-trifluoromethylphenoxy)-but-1'''(t)-en-1'''-yl]cyclopent-1'α-yl} acetaldehyde 1,2'-hemiacetal in 35 ml. of anhydrous ether is then added, and the reaction mixture is kept at room temperature for 60 hours. Water is then slowly added until the precipitate is dissolved, the aqueous phase is separated and acidified with 3.3 g. (26.2 mmoles) of oxalic acid dissolved in water. The product is extracted with ether and the organic extract is washed with saturated sodium chloride solution, dried over magnesium sulfate and evaporated to dryness under vacuum. The residue is treated with an excess of ethereal diazomethane for 15 minutes, evaporated to dryness, redissolved in ether and washed with a saturated sodium chloride solution, dried over anhydrous magnesium sulfate and evaporated to dryness under vacuum. The residue is purified by t.l.c. using ethyl acetate:methylene chloride (3:7), to yield 1.33 g. of dl 6ξ,9α-dihydroxy-11α,15α-bistetrahydropyranyloxy-16-m-trifluoromethylphenoxy-17,18,19,20-tetranorprost-4-yn-13-trans-enoic acid methyl ester (racemic VII-A, $R^2$ = m-$CF_3$), as an oil, which has the following constants:

U.V. $\lambda_{max}^{MeOH}$ 220, 275, 280–284 nm (log ϵ3.92, 3.29, 3.20) (ϵ8300, 1950, 1660);
I.R. $\nu_{max}^{CHCl_3}$ 3620, 3490, 3320, 1740, 1595 cm$^{-1}$;
N.M.R. $\delta TMS^{CDCl_3}$ 3.83 (s, 3H, methyl ester);
5.33–5.83 (m, 2H, H-13,14);
6.93–7.33 (m, 4H, aromatic).

In a similar manner, starting from 1.825 g. of dl {2'α-hydroxy-4'α-tetrahydropyranyloxy-5'β-[3''β-tetrahydropyranyloxy-4''-(m-trifluoromethylphenoxy)-but-1''(t)-en-1'''-yl]cyclopent-1'α-yl} acetaldehyde 1,2'-hemiacetal there are obtained 1.465 g. of dl 6ξ,9α-dihydroxy-11α,15β-bistetrahydropyranyloxy-16-m-trifluoromethylphenoxy-17,18,19,20-tetranorprost-4-yn-13-trans-enoic acid methyl ester (racemic VII-B, $R^2$ = m-$CF_3$), an oil, which has the following constants:

U.V. $\epsilon_{max}^{MeOH}$ 222, 275, 280–284 nm (log ϵ 3.91, 3.29, 3.24) (ϵ 8120, 1950, 1740);
I.R. $\nu_{max}^{CHCl_3}$ 3630, 3480, 3320, 1740, 1595 cm$^{-1}$;
N.M.R. $\delta_{TMS}^{CDCl_3}$ 3.63 (s, 3H, methyl ester);
5.40–5.80 (m, 2H, H-13,14);
6.97–7.37 (m, 4H, aromatic).

Likewise, 1'R-{2'α-hydroxy-4'α-tetrahydropyranyloxy-5'β-[3''α-tetrahydropyranyloxy-4''-(m-trifluoromethylphenoxy)-but-1'''(t)-en-1'''-yl]cyclopent-1'α-yl } acetaldehyde, 1,2'-hemiacetal and 1'R-{2'α-hydroxy -4'α-tetrahydropyranyloxy-5'β-[3'λ'β-tetrahydropyranyloxy-4''-(m-trifluoromethylphenoxy)-but-1'''(t)-en-1'''-yl]cyclopent-1'α-yl } acetaldehyde 1,2'-hemiacetal are converted respectively into 8R-6ξ,9α-dihydroxy-11α,15α-bistetrahydropyranyloxy-16-m-trifluoromethylphenoxy-17,18,19,20-tetranorprost-4-yn-13-trans-enoic acid methyl ester (8R-antimer of VII-A, $R^2$ = m-$CF_3$) and 8R-6ξ,9α-dihydroxy-11α,15β-bistetrahydropyranyloxy-16-m-trifluoromethylphenoxy-17,,18,19,20-tetranorprost-4-yn-13-trans-enoic acid methyl ester (8R-antimer of VII-B, $R^2$ = m-$CF_3$).

EXAMPLE 9

To a solution of 1.31 g. (2 mmoles) of dl 6ξ,9α-dihydroxy-11α,15α-bistetrahydropyranyloxy-16-m-trifluoromethylphenoxy-17,18,19,20-tetranorprost-4-yn-13-trans-enoic acid methyl ester in 25 ml. of anhydrous methylene chloride are added 4.48 ml. (32 mmoles) of anhydrous triethylamine, 2.71 ml. (28.7 mmoles) of acetic anhydride and 27.3 mg. (0.2235 mmoles) of 4-dimethylaminopyridine. The resulting mixture is stirred at room temperature for 1 hour, and passed through a column of Florisil (200 g.) in methylene chloride, eluting the product with methylene chloride and methylene chloride-ethyl acetate (9:1). The combined eluates are evaporated to dryness under reduced pressure and the residue purified by thin layer chromatography using ethyl acetate: methylene chloride (15:85) as gradient, thus obtaining 1.260 g of dl 6ξ,9α-diacetoxy-11α,15α-bistetrahydropyranyloxy-16-m-trifluoromethylphenoxy-17,18,19,20-tetranorprost-4-yn-13-trans-enoic acid methyl ester (racemic VIII-A, $R^2$ = m-$CF_3$), as an oil, which has the following constants:

U.V. $\lambda_{max}^{meOH}$ 222, 275–276, 280–283 nm (log ϵ 3.96, 3.32, 3.32) (ϵ 9100, 2090, 2090);

I.R. $\nu_{max}^{CHCl_3}$ 3320, 1740, 1595 cm$^{-1}$;
N.M.R. $\delta_{TMS}^{CDCl_3}$ 1.95, 2.00, 2.03, 2.07 (m, 2 × acetoxy H);
 2.47 (s, 2H, H-2);
 3.65 (s, 3H, methyl ester);
 5.50–5.83 (m, 2H, H-13,14);
 6.95–7.33 (m, 4H, aromatic).

In a similar manner, starting from 1.435 g. of dl 6ξ,9α-dihydroxy-11α,15β-bistetrahydropyranyloxy-16-m-trifluoromethylphenoxy-17,18,19,20-tetranorprost-4-yn-13-trans-enoic acid methyl ester there are obtained 1.47 g. of dl 6ξ,9α-diacetoxy-11α,15β-bistetrahydropyranyloxy-16-m-trifluoromethylphenoxy-17,18,29,20-tetranorprost-4-yn-13-trans-enoic acid methyl ester (racemic VIII-B, R$^2$ = m-CF$_3$), as an oil, which has the following constants:
U.V. $\nu_{max}^{MeOH}$ 222, 275, 280–283 nm (log ε 3.96, 3.29, 3.29) (ε 9100, 1950, 1950);
I.R. $\nu_{max}^{CHCl_3}$ 3320, 1740, 1595 cm$^{-1}$;
N.M.R. $\delta_{TMS}^{CDCl_3}$ 2.00, 2.05 (m, 2 × acetoxy H);
 2.47 (s, 2H, H-2);
 3.63 (s, 3H, methyl ester);
 5.47–5.80 (m, 2H, H-13,14);
 6.97–7.33 (m, 4H, aromatic).

By the same method, starting from 8R-6ξ,9α-dihydroxy-11α,15α-bistetrahydropyranyloxy-16-m-trifluoromethylphenoxy-17,18,19,20-tetranorprost-4-yn-13-trans-enoic acid methyl ester and 8R-6ξ,9α-dihydroxy-11α,15β-bis-tetrahydropyranyloxy-16-m-trifluoromethylphenoxy-17,18,19,20-tetranorprost-4-yn-13-trans-enoic acid methyl ester there are respectively obtained: 8R-6ξ,9α-diacetoxy-11α,15α-bistetrahydropyranyloxy-16-m-trifluoromethylphenoxy-17,18,19,20-tetranorprost-4-yn-13-trans-enoic acid methyl ester (8R-antimer of VIII-A, R$^2$ = m-CF$_3$) and 8R-6ξ,9α-diacetoxy-11α,15β-bistetrahydropyranyloxy-16-m-trifluoromethylphenoxy-17,18,19,20-tetranorprost-4-yn-13-trans-enoic acid methyl ester (8R-antimer of VIII-B, R$^2$ = m-CF$_3$).

EXAMPLE 10

A mixture of 1.412 g. (7.415 mmoles) of cuprous iodide and 10 ml. of diethyl ether is cooled to −10° C. To the stirred cold mixture is added, under argon atmosphere, a solution of ethereal methyllithium until the reaction mixture becomes slightly yellow. The solution is then cooled to −78° C and then a solution of 1.095 g. (1.483 mmoles) of dl 6ξ,9α-diacetoxy-11α,15α-bistetrahydropyranyl-oxy-16-m-trifluoromethylphenoxy-17,18,19,20-tetranorprost-4-yn-13-trans-enoic acid methyl ester in 25 ml of diethyl ether is added. The reaction mixture is maintained under the same conditions for 4 ½ hours, saturated aqueous ammonium chloride solution is then added and the reaction mixture is allowed to attain room temperature. The mixture is stirred for 1 hour further, filtered through Celite (diatomaceous earth) and the filtrate is washed with saturated sodium chloride solution, dried over anhydrous magnesium sulfate and evaporated to dryness. The residue is chromatographed on 200 g. of Florisil. The fractions eluted with ethyl acetate:methylene chloride mixtures (1:9 and 2:8) afford 649 mg. of dl 9α-acetoxy-11α,15α-bistetrahydropyranyloxy-16-m-trifluoromethylphenoxy-17,18,19,20-tetranorprosta-4,5,13-trans-trienoic acid methyl ester (racemic IX-A, R$^2$ = m-CF$_3$), as an oil, which has the following constants:

U.V. $\lambda_{max}^{MeOH}$ 221.5, 275, 282 nm (log ε 3.94, 3.34, 3.30) (ε 8700, 2180, 1990);
I.R. $\nu_{max}^{CHCl_3}$ 1980, 1735, 1595 cm$^{-1}$;
N.M.R. $\delta_{TMS}^{CDCl_3}$ 2.02 (s, 3H, acetate);
 3.30 (s, 3H, methyl ester);
 5.37–5.80 (m, 2H, H-13,14);
 6.97–7.35 (m, 4H, aromatic).

In a similar manner but using dl 6ξ,9α-diacetoxy-11α,15β-bistetrahydropyranyloxy-16-m-trifluoromethylphenoxy-17,18,19,20-tetranorprost-4-yn-13-trans-enoic acid methyl ester there is obtained dl 9α-acetoxy-11α,15β-bistetrahydropyranyloxy-16-m-trifluoromethylphenoxy-17,18,19,20-tetranorprosta-4,5,13-trans-trienoic acid methyl ester (racemic IX-B, R$^2$ = m-CF$_3$), as an oil, which has the following constants:
U.V. $\lambda_{max}^{MeOH}$ 222, 275, 282 nm (log ε 3.89, 3.21, 3.13) (ε 7750, 1620, 1350);
I.R. $\nu_{max}^{CHCl_3}$ 1980, 1740, 1595 cm$^{-1}$;
N.M.R. $\delta_{TMS}^{CDCl_3}$ 2.02 (s, 3H, acetate);
 3.62 (s, 3H, methyl ester);
 5.43–5.80 (m, 2H, H-13,14);
 6.97–7.33 (m, 4H, aromatic).

By the same method, 8R-6ξ,9α-diacetoxy-11α,15α-bistetrahydropyranyloxy-16-m-trifluoromethylphenoxy-17,18,19,20-tetranorprost-4-yn-13-trans-enoic acid methyl ester and 8R-6ξ,9α-diacetoxy-11α,15β-bistetrahydropyranyloxy-16-m-trifluoromethylphenoxy-17,18,19,20-tetranorprost-4-yn-13-trans-enoic acid methyl ester are converted respectively into 8R-9α-acetoxy-11α,15α-bistetrahydropyranyloxy-16-m-trifluoromethylphenoxy-17,18,19,20-tetranorprosta-4,5,13-trans-trienoic acid methyl ester (8R-antimer of IX-A, R$^2$ = m-CF$_3$) and 8R-9α-acetoxy-11α,15β-bistetrahydropyranyloxy-16-m-trifluoromethylphenoxy-17,18,19,20-tetranorprosta-4,5,13-trans-trienoic acid methyl ester (8R-antimer of IX-B, R$^2$ = m-CF$_3$).

EXAMPLE 11

A solution of 614 mg. (0.91 mmoles) of dl 9α-acetoxy-11α,15α-bistetrahydropyranyloxy-16-m-trifluoromethylphenoxy-17,18,19,20-tetranorprosta-4,5,13-trans-trienoic acid methyl ester in 7 ml. of 70% aqueous acetic acid is stirred at room temperature for 14 hours. The reaction mixture is then evaporated to dryness under reduced pressure, eliminating the excess acid by distillation with chloroform. The residue is purified by t.l.c. using ethyl acetate:methylene chloride (6:4) as eluant, thus obtaining 398 mg. of dl 9α-acetoxy-11α,15α-dihydroxy-16-m-trifluoromethylphenoxy-17,18,19,20-tetranorprosta-4,5,13-trans-trienoic acid methyl ester (racemic X-A, R$^2$ = m-CF$_3$), as an oil, which has the following constants:
U.V. $\lambda_{max}^{MeOH}$ 221, 275, 279–282 nm (log ε 3.937, 3.326, 3.24) (ε 8630, 2120, 1740);
I.R. $\nu_{max}^{CHCl_3}$ 3610, 3440, 1980, 1740, 1595 cm$^{-1}$;
N.M.R. $\delta_{TMS}^{CDCl_3}$ 2.05 (s, 3H, acetate);
 3.62 (s, 3H, methyl ester);
 3.73–4.10 (m, 3H, H-11,6);
 4.30–4.67 (m, 1H, H-15);
 4.77–5.27 (m, 3H, H-4,6,9);
 5.50–5.77 (m, 2H, H-13,14);
 6.93–7.39 (m, 4H, aromatic).

In a similar manner starting from 592 mg. of dl 9α-acetoxy-11α,15β-bistetrahydropyranyloxy-16-m-trifluoromethylphenoxy-17,18,19,20-tetranorprosta-4,5,13-trans-trienoic acid methyl ester there are obtained 402 mg. of dl 9α-acetoxy-11α,15β-dihydroxy-16-m-trifluoromethylphenoxy-17,18,19,20-tetranorprosta-4,5,13-trans-trienoic acid methyl ester (racemic X-B, $R^2$ = m-CF$_3$) as an oil, which has the following constants:

U.V. $\lambda_{max}^{MeOH}$ 222, 275, 282 nm (log $\epsilon$ 3.925, 3.276, 3.22) ($\epsilon$ 8400, 1880, 1660);
I.R. $\nu_{max}^{CHCl_3}$ 3620, 3440, 1980, 1740, 1595 cm$^{-1}$;
N.M.R. $\delta$TMS$^{CDCl_3}$ 2.05 (s, 3H, acetate);
  3.72 (s, 3H, methyl ester);
  3.73–4.13 (m, 3H, H-11,16);
  4.17–4.70 (m, 1H, H-15);
  4.70–5.33 (m, 3H, H-4,6,9);
  5.53–5.80 (m, 2H, H-13,14);
  6.93–7.40 (m, 4H, aromatic);
M.S. (as bis-trimethylsilyl ether) m/e 656 (M$^+$).

By the same method 8R-9α-acetoxy-11α,15α-bistetrahydropyranyloxy-16-m-trifluoromethylphenoxy-17,18,19,20-tetranorprosta-4,5,13-trans-trienoic acid methyl ester and 8R-9α-acetoxy-11α,15β-bistetrahydropyranyloxy-16-m-trifluoromethylphenoxy-17,18,19,20-tetranorprosta-4,5,13-trans-trienoic acid methyl ester are converted respectively into 8R-9α-acetoxy-11α,15α-dihydroxy-16-m-trifluoromethylphenoxy-17,18,19,20-tetranorprosta-4,5,13-trans-trienoic acid methyl ester (8R-antimer of X-A, $R^2$ = m-CF$_3$) and 8R-9α-acetoxy-11α,15β-dihydroxy-16-m-trifluoromethylphenoxy-17,18,19,20-tetranorprosta-4,5,13-trans-trienoic acid methyl ester (8R-antimer of X-B, $R^2$ = m-CF$_3$).

EXAMPLE 12

To a solution of 203 mg. (0.445 mmoles) of dl 9α-acetoxy-11α,15α-dihydroxy-16-m-trifluoromethylphenoxy-17,18,19,20-tetranorprosta-4,5,13-trans-trienoic acid methyl ester in 8.7 ml. of methanol there are added 1.45 ml. of water and 203 mg. (1.47 mmoles) of anhydrous potassium carbonate, and the resulting mixture is stirred at room temperature for 40 hours. The solvent is eliminated under reduced pressure and the residue diluted with water and extracted with methylene chloride (3 × 20 ml.) to eliminate unsaponifiable products. The aqueous solution is saturated with sodium potassium tartrate, 20 ml. of ethyl acetate are added and the mixture is cooled to 0° C; there are then added 232 mg. (1.84 mmoles) of oxalic acid dissolved in 2 ml. of water, under stirring, the aqueous phase is separated and extracted with cold ethyl acetate (2 × 20 ml.), the combined organic extracts are washed with a saturated sodium potassium tartrate solution (3 × 7 ml.), dried over anhydrous magnesium sulfate and evaporated to dryness under reduced pressure, thus obtaining 166 mg. of dl 9α,11α,15α-trihydroxy-16-m-trifluoromethylphenoxy-17,18,19,20-tetranorprosta-4,5,13-trans-trienoic acid (racemic XI-A, $R^2$ = m-CF$_3$), as an oil, which has the following constants:

U.V. $\lambda_{max}^{MeOH}$ 221, 275, 282 nm (log. $\epsilon$ 3.96, 3.33, 3.28) ($\epsilon$ 9100, 2140, 1900);
I.R. $\nu_{max}^{CHCl_3}$ 3400, 1975, 1720, 1595 cm$^{-1}$;
N.M.R. $\delta_{TMS}^{CDCl_3}$ 3.85–4.10 (m, 3H);
  4.98–5.30 (m, 2H, H-4,6);
  5.60–5.77 (m, 2H, H-13,14);
  6.98–7.40 (m, 4H, aromatic);
C-13 N.M.R. $\delta$(ppm) 176.688 (C-1); 91.123 (C-4); 204.289 (C-5); 90.018 (C-6); 72.333 (C-9); 77.632 (C-11); 130.037 (C-13); 135.466 (C-14); 71.910 (C-15); 71.033 (C-16);
M.S. (as methyl ester tris-trimethylsilyl ether) m/e 686 (M$^+$).

In a similar manner starting from 201 mg. (0.441 mmoles) of dl 9α-acetoxy-11α,15β-dihydroxy-16-m-trifluoromethylphenoxy-17,18,19,20-tetranorprosta-4,5,13-trans-trienoic acid methyl ester there are obtained 163 mg. of dl 9α,11α,15β-trihydroxy-16-m-trifluoromethylphenoxy-17,18,19,20-tetranorprosta-4,5,13-trans-trienoic acid (racemic XI-B, $R^2$ = m-CF$_3$), as an oil, which has the following constants:

U.V. $\lambda_{max}^{MeOH}$ 221.5, 275, 282 nm (log $\epsilon$ 3.96, 3.35, 3.30); ($\epsilon$ 9100, 2240, 1990);
I.R. $\nu_{max}^{CHCl_3}$ 3420, 1975, 1720, 1595 cm$^{-1}$;
N.M.R. $\delta_{TMS}^{CDCl_3}$ 3.85–410 (m, 3H, H-16); 4.15–4.35 (m, 1H); 4.40–4.65 (m, 1H); 5.00–5.30 (m, 2H, H-4,6); 5.60–5.80 (m, 2H, H-13, 14); 7.00–7.45 (m, 4H, aromatic);
M.S. (as methyl ester tris-trimethylsilyl ether) m/e 686 (M$^+$).
C-13 N.M.R $\delta$(ppm) 176.331 (C-1); 91.286 (C-4); 204.321 (C-5); 90.278, 89.986 (C-6); 72.886, 72.561 (C-9); 77.892 (C-11); 129.062 (C-13); 135.401 (C-14); 71.975 (C-15); 70.838 (C-16).

By the same method, 8R-9α-acetoxy-11α, 15α-dihydroxy-16-m-trifluoromethylphenoxy-17,18,19,20-tetranorprosta-4,5,13-trans-trienoic acid methyl ester and 8R-9α-acetoxy-11α,15β-dihydroxy-16-m-trifluoromethylphenoxy-17,18,19,20-tetranorprosta-4,5,13-trans-trienoic acid methyl ester are converted respectively into 8R-9α,11α,15α-trihydroxy-16-m-trifluormethylphenoxy-17,18,19,20-tetranorprosta-4,5,13-trans-trienoic acid (8R-antimer of XI-A, $R^2$ = m-CF$_3$) and 8R-9α,11α,15β-trihydroxy-16-m-trifluoromethylphenoxy-17,18,19,20-tetranorprosta-4,5,13-trans-trienoic acid (8R-antimer of XI-B, $R^2$ = m-CF$_3$).

EXAMPLE 13

A. By following the method of Example 1, part A, substituting:
  o-trifluoromethylphenol,
  p-trifluoromethylphenol,
  o-bromophenol,
  m-bromophenol,
  o-fluorophenol,
  m-fluorophenol,
  p-butylphenol,
  o-ethoxyphenol,
  m-ethoxyphenol and
  p-ethylphenol for m-trifluoromethylphenol there are respectively obtained:
  ethyl o-trifluoromethylphenoxyacetate,
  ethyl p-trifluoromethylphenoxyacetate,
  ethyl o-bromophenoxyacetate,
  ethyl m-bromophenoxyacetate,
  ethyl o-fluorophenoxyacetate,
  ethyl m-fluorophenoxyacetate,
  ethyl p-butylphenoxyacetate,
  ethyl o-ethoxyphenoxyacetate,
  ethyl m-ethoxyphenoxyacetate and
  ethyl p-ethylphenoxyacetate.

B. A mixture of 30 g. of phenoxyacetic acid, 100 ml. of ethanol and 10 ml. of sulfuric acid is refluxed for 22 hours, cooled, poured into ice water and extracted with methylene chloride. The organic extract is washed with water to neutrality, dried over sodium sulfate and evaporated to dryness under vacuum, to yield ethyl phenoxyacetate, b.p. 123°/17 mm.Hg.

In a similar manner starting from the corresponding free acids, there are obtained:
  ethyl o-methoxyphenoxyacetate, ethyl m-methoxyphenoxyacetate,
ethyl p-methoxyphenoxyacetate,
ethyl p-ethoxyphenoxyacetate,
ethyl o-methylphenoxyacetate,
ethyl m-methylphenoxyacetate,
ethyl p-fluorophenoxyacetate,
ethyl o-chlorophenoxyacetate,
ethyl m-chlorophenoxyacetate, and
ethyl p-chlorophenoxyacetate.

C. By repeating the procedure described in part B of Example 1, using as starting materials the compounds obtained in parts A and B of this Example, there are respectively obtained:

dimethyl 2-oxo-3-(o-trifluoromethylphenoxy)propylphosphonate,
dimethyl 2-oxo-3-(p-trifluoromethylphenoxy)propylphosphonate,
dimethyl 2-oxo-3-(o-bromophenoxy)propylphosphonate,
dimethyl 2-oxo-3-(m-bromophenoxy)propylphosphonate,
dimethyl 2-oxo-3-(o-fluorophenoxy)propylphosphonate,
dimethyl 2-oxo-3-(m-fluorophenoxy)propylphosphonate,
dimethyl 2-oxo-3-(p-butylphenoxy)propylphosphonate,
dimethyl 2-oxo-3-(o-ethoxyphenoxy)propylphosphonate,
dimethyl 2-oxo-3-(m-ethoxyphenoxy)propylphosphonate,
dimethyl 2-oxo-3-(p-ethylphenoxy)propylphosphonate,
dimethyl 2-oxo-3-(phenoxy)propylphosphonate,
dimethyl 2-oxo-3-(o-methoxyphenoxy)propylphosphonate,
dimethyl 2-oxo-3-(m-methoxyphenoxy)propylphosphonate,
dimethyl 2-oxo-3-(p-methoxyphenoxy)propylphosphonate,
dimethyl 2-oxo-3-(p-ethoxyphenoxy)propylphosphonate,
dimethyl 2-oxo-3-(o-methylphenoxy)propylphosphonate,
dimethyl 2-oxo-3-(m-methylphenoxy)propylphosphonate,
dimethyl-2-oxo-3-(p-fluorophenoxy)propylphosphonate,
dimethyl 2-oxo-3-(o-chlorophenoxy)propylphosphonate,
dimethyl 2-oxo-3-(m-chlorophenoxy)propylphosphonate and
dimethyl 2-oxo-3-(p-chlorophenoxy)propylphosphonate.

D. In accordance with the method described in Example 1, part C, dl (2'α-hydroxy-4'α-p-phenylbenzoyloxy-5'β-formylcyclopent-1'α-yl)acetic acid 1,2'-lactone is condensed with the propylphosphonate reagents obtained in part C of this Example, to produce, respectively:

dl {2'α-hydroxy-4'α-p-phenylbenzoyloxy-5'β-[3''-oxo-4''-(o-trifluoromethylphenoxy)-but-1''(t)-en-1''-yl]cyclopent-1'α-yl} acetic acid 1,2'-lactone,
dl {2'α-hydroxy-4'α-p-phenylbenzoyloxy-5'β-[3''-oxo-4''-(p-trifluoromethylphenoxy)-but-1''(t)-en-1''-yl]cyclopent-1'α-yl} acetic acid 1,2'-lactone,
dl {2'α-hydroxy-4'α-p-phenylbenzoyloxy-5'β-[3''-oxo-4''-(o-bromophenoxy)-but-1''(t)-en-1''-yl]cyclopent-1'α-yl} acetic acid 1,2'-lactone,
dl {2'α-hydroxy-4'α-p-phenylbenzoyloxy-5'β-[3''-oxo-4''-(m-bromophenoxy)-but-1''(t)-en-1''-yl]cyclopent-1'α-yl} acetic acid 1,2'-lactone,
dl {2'α-hydroxy-4'α-p-phenylbenzoyloxy-5'β-[3''-oxo-4''-(o-fluorophenoxy)-but-1''(t)-en-1''-yl]cyclopent-1'α-yl} acetic acid 1,2'-lactone,
dl {2'α-hydroxy-4'α-p-phenylbenzoyloxy-5'β-[3''-oxo-4''-(m-fluorophenoxy)-but-1''(t)-en-1''-yl]cyclopent-1'α-yl } acetic acid 1,2'-lactone,
dl {2'α-hydroxy-4'α-p-phenylbenzoyloxy-5'β-[3''-oxo-4''-(p-butylphenoxy)-but-1''(t)-en-1''yl]cyclopent-1'α-yl} acetic acid 1,2'-lactone,
dl {2'α-hydroxy-4'α-p-phenylbenzoyloxy-5'β-[3''-oxo-4''-(o-ethoxyphenoxy)-but-1''(t)-en-1''-yl]cyclopent-1'α-yl} acetic acid 1,2'-lactone,
dl {2'α-hydroxy-4'α-p-phenylbenzoyloxy-5'β-[3''-oxo-4''-(m-ethoxyphenoxy)-but-1''(t)-en-1''-yl]cyclopent-1'α-yl} acetic acid 1,2'-lactone,
dl {2'α-hydroxy-4'α-p-phenylbenzoyloxy-5'β-[3''-oxo-4''-(p-ethylphenoxy)-but-1''(t)-en-1''-yl]cyclopent-1'α-yl} acetic acid 1,2'-lactone,
dl{2'α-hydroxy-4'α-p-phenylbenzoyloxy-5'β-[3''-oxo-4''-(phenoxy)-but-1''(t)-en-1''-yl]cyclopent-1'α-yl}acetic acid 1,2'-lactone,
dl{2'α-hydroxy-4'α-p-phenylbenzoyloxy-5'β-[3''-oxo-4''-(o-methoxyphenoxy)-but-1''(t)-en-1''-yl]cyclopent-1'α-yl} acetic acid 1,2'-lactone,
dl{2'α-hydroxy-4'α-p-phenylbenzoyloxy-5'β-[3''-oxo-4''-(m-methoxyphenoxy)-but-1''(t)-en-1''-yl]cyclopent-1'α-yl} acetic acid 1,2'-lactone,
dl{2'α-hydroxy-4'α-p-phenylbenzoyloxy-5'β-[3''-oxo-4''-(p-methoxyphenoxy)-but-1''(t)-en-1''-yl]cyclopent-1'α-yl} acetic acid 1,2'-lactone,
dl{2'α-hydroxy-4'α-p-phenylbenzoyloxy-5'β-[3''-oxo-4''-(p-ethoxyphenoxy)-but1''(t)-en-1''-yl]cyclopent-1'α-yl} acetic acid 1,2'-lactone,
dl{2'α-hydroxy-4'α-p-phenylbenzoyloxy-5'β-[3''-oxo-4''-(o-methylphenoxy)-but-1''(t)-en-1''-yl]cyclopent-1'α-yl} acetic acid 1,2'-lactone,
dl{2'α-hydroxy-4'α-p-phenylbenzoyloxy-5'β-[3''-oxo-4''-(m-methylphenoxy)-but-1''(t)-en-1''-yl]cyclopent-1'α-yl} acetic acid 1,2'-lactone,
dl{2'α-hydroxy-4'α-p-phenylbenzoyloxy-5'β-[3''-oxo-4''-(p-fluorophenoxy)-but-1''(t)-en-1''-yl]cyclopent-1'α-yl} acetic acid 1,2'-lactone,
dl{2'α-hydroxy-4'α-p-phenylbenzoyloxy-5'β-[3''-oxo-4''-(o-chlorophenoxy)-but-1''(t)-en-1''-yl]cyclopent-1'α-yl} acetic acid 1,2'-lactone,
dl{2'α-hydroxy-4'α-p-phenylbenzoyloxy-5'β-[3''-oxo-4''-(m-chlorophenoxy)-but-1''(t)-en-1''-yl]cyclopent-1'α-yl } acetic acid 1,2'-lactone and
dl{2'α-hydroxy-4'α-p-phenylbenzoyloxy-5'β-[3''-oxo-4''-(p-chlorophenoxy)-but-1''(t)-en-1''-yl]cyclopent-1'α-yl} acetic acid 1,2'-lactone.

In a similar manner, starting from 1'R-(2'α-hydroxy-4'α-p-phenylbenzoyloxy-5'β-formylcyclopent-1'α-yl)acetic acid 1,2'-lactone there are obtained the corresponding 1'R-antimeric derivatives of the above-listed dl compounds.

EXAMPLE 14

Example 2 is repeated using as starting materials the dl compounds obtained in Example 13 to produce, respectively:

dl{2′α-hydroxy-4′α-p-phenylbenzoyloxy-5′β-[3″α-hydroxy-4″-(o-trifluoromethylphenoxy)-but-1‴(t)-en-1‴-yl] cyclopent-1′α-yl} acetic acid 1,2′-lactone and dl{2′α-hydroxy-4′α-p-phenylbenzoyloxy-5′β-[3″β-hydroxy-4″-(o-trifluoromethylphenoxy)-but-1‴(t)-en-1‴-yl]cyclopent-1′α-yl} acetic acid 1,2′-lactone;

dl{2′α-hydroxy-4′α-p-phenylbenzoyloxy-5′β-[3″α-hydroxy-4″-(p-trifluoromethylphenoxy)-but-1‴(t)-en-1‴-yl] cyclopent-1′α-yl} acetic acid 1,2′-lactone and dl{2′α-hydroxy-4′α-p-phenylbenzoyloxy-5′β-[3″β-hydroxy-4″-(p-trifluoromethylphenoxy)-but-1‴(t)-en-1‴yl]cyclopent-1′α-yl} acetic acid 1,2′-lactone;

dl{2′α-hydroxy-4′α-p-phenylbenzoyloxy-5′β-[3″α-hydroxy-4″-(o-bromophenoxy)-but-1‴(t)-en-1‴-yl]cyclopent-1′α-yl} acetic acid 1,2′-lactone and dl{2′α-hydroxy-4′α-p-phenylbenzoyloxy-5′β-[3″β-hydroxy-4″-(o-bromophenoxy)-but-1‴(t)-en-1‴-yl]cyclopent-1′α-yl} acetic acid 1,2′-lactone;

dl{2′α-hydroxy-4′α-p-phenylbenzoyloxy-5′β-[3″α-hydroxy-4″-(m-bromophenoxy)-but-1‴(t)-en-1‴-yl]cyclopent-1′α-yl} acetic acid 1,2′-lactone and dl{2′α-hydroxy-4′α-p-phenylbenzoyloxy-5′β-[3″β-hydroxy-4″-(m-bromophenoxy)-but-1‴(t)-en-1‴-yl]cyclopent-1′α-yl} acetic acid 1,2′-lactone;

dl{2′α-hydroxy-4′α-p-phenylbenzoyloxy-5′β-[3″α-hydroxy-4″-(o-fluorophenoxy)-but-1‴(t)-en-1‴-yl]cyclopent-1′α-yl} acetic acid 1,2′-lactone and dl{2′α-hydroxy-4′α-p-phenylbenzoyloxy-5′β-[3″β-hydroxy-4″-(o-fluorophenoxy)-but-1‴(t)-en-1‴-yl]cyclopent-1′α-yl} acetic acid 1,2′-lactone;

dl{2′α-hydroxy-4′α-p-phenylbenzoyloxy-5′β-[3″α-hydroxy-4″-(m-fluorophenoxy)-but-1‴(t)-en-1‴-yl]cyclopent-1′α-yl} acetic acid 1,2′-lactone and dl{2′α-hydroxy-4′α-p-phenylbenzoyloxy-5′β-[3″β-hydroxy-4″-(m-fluorophenoxy)-but-1‴(t)-en-1‴-yl]cyclopent-1′α-yl} acetic acid 1,2′-lactone;

dl{2′α-hydroxy-4′α-p-phenylbenzoyloxy-5′β-[3″α-hydroxy-4″-(p-butylphenoxy)-but-1‴(t)-en-1‴-yl]cyclopent-1′α-yl} acetic acid 1,2′-lactone and dl{2′α-hydroxy-4′α-p-phenylbenzoyloxy-5′β-[3″β-hydroxy-4″-(p-butylphenoxy)-but-1‴(t)-en-1‴-yl]cyclopent-1′α-yl} acetic acid 1,2′-lactone;

dl{2′α-hydroxy-4′α-p-phenylbenzoyloxy-5′β-[3″α-hydroxy-4″-(o-ethoxyphenoxy)-but-1‴(t)-en-1‴-yl]cyclopent-1′α-yl} acetic acid 1,2′-lactone and dl{2′α-hydroxy-4′α-p-phenylbenzoyloxy-5′β-[3″β-hydroxy-4″-(o-ethoxyphenoxy)-but-1‴(t)-en-1‴-yl]cyclopent-1′α-yl} acetic acid 1,2′-lactone;

dl{2′α-hydroxy-4′α-p-phenylbenzoyloxy-5′β-[3″α-hydroxy-4″-(m-ethoxyphenoxy)-but-1‴(t)-en-1‴-yl]cyclopent-1′α-yl} acetic acid 1,2′-lactone and dl{2′α-hydroxy-4′α-p-phenylbenzoyloxy-5′β-[3″β-hydroxy-4″-(m-ethoxyphenoxy)-but-1‴(t)-en-1‴-yl]cyclopent-1′α-yl} acetic acid 1,2′-lactone;

dl{2′α-hydroxy-4′α-p-phenylbenzoyloxy-5′β-[3″α-hydroxy-4″-(p-ethylphenoxy)-but-1‴(t)-en-1‴-yl]cyclopent-1′α-yl} acetic acid 1,2′-lactone and dl{2′α-hydroxy-4′α-p-phenyl benzoyloxy-5′β-[3″β-hydroxy-4″-(p-ethylphenoxy)-but-1‴(t)-en-1‴-yl]cyclopent-1′α-yl} acetic acid 1,2′-lactone;

dl{2′α-hydroxy-4′α-p-phenylbenzoyloxy-5′β-[3″α-hydroxy-4″-(phenoxy)-but-1‴(t)-en-1‴-yl]cyclopent-1′α-yl} acetic acid 1,2′-lactone and dl{2′α-hydroxy-4′α-p-phenylbenzoyloxy-5′β-[3″β-hydroxy-4″-(phenoxy)-but-1‴(t)-en-1‴-yl]cyclopent-1′α-yl} acetic acid 1,2′-lactone;

dl{2′α-hydroxy-4′α-p-phenylbenzoyloxy-5′β-[3″α-hydroxy-4″-(o-methoxyphenoxy)-but-1‴(t)-en-1‴-yl]cyclopent-1′α-yl} acetic acid 1,2′-lactone and dl{2′α-hydroxy-4′α-p-phenylbenzoyloxy-5′β-[3″β-hydroxy-4″-(o-methoxyphenoxy)-but-1‴(t)-en-1‴-yl]cyclopent-1′α-yl} acetic acid 1,2′-lactone;

dl{2′α-hydroxy-4′α-p-phenylbenzoyloxy-5′β-[3″α-hydroxy-4″-(m-methoxyphenoxy)-but-1‴(t)-en-1‴-yl]cyclopent-1′α-yl} acetic acid 1,2′-lactone and dl{2′α-hydroxy-4′α-p-phenylbenzoyloxy-5′β-[3″β-hydroxy-4″-(m-methoxyphenoxy)-but-1‴(t)-en-1‴-yl]cyclopent-1′α-yl} acetic acid 1,2′-lactone;

dl{2′α-hydroxy-4′α-p-phenylbenzoyloxy-5′β-[3″α-hydroxy-4″-(p-methoxyphenoxy)-but-1‴(t)-en-1‴-yl]cyclopent-1′α-yl} acetic acid 1,2′-lactone and dl{2′α-hydroxy-4′α-p-phenylbenzoyloxy-5′β-[3″β-hydroxy-4″-(p-methoxyphenoxy)-but-1‴(t)-en-1‴-yl]cyclopent-1′α-yl} acetic acid 1,2′-lactone;

dl{2′α-hydroxy-4′α-p-phenylbenzoyloxy-5′β-[3″α-hydroxy-4″-(p-ethoxyphenoxy)-but-1‴(t)-en-1‴-yl]cyclopent-1′α-yl} acetic acid 1,2′-lactone and dl{2′α-hydroxy-4′α-p-phenylbenzoyloxy-5′β-[3″β-hydroxy-4″-(p-ethoxyphenoxy)-but-1‴(t)-en-1‴-yl]cyclopent-1′α-yl} acetic acid 1,2′-lactone;

dl{2′α-hydroxy-4′α-p-phenylbenzoyloxy-5′β-[3″α-hydroxy-4″-(o-methylphenoxy)-but-1‴(t)-en-1‴-yl]cyclopent-1′α-yl} acetic acid 1,2′-lactone and dl{2′α-hydroxy-4′α-p-phenylbenzoyloxy-5′β-[3″β-hydroxy-4″-(o-methylphenoxy)-but-1‴(t)-en-1‴-yl]cyclopent-1′α-yl} acetic acid 1,2′-lactone;

dl{2′α-hydroxy-4′α-p-phenylbenzoyloxy-5′β-[3″α-hydroxy-4″-(m-methylphenoxy)-but-1‴(t)-en-1‴-yl]cyclopent-1′α-yl} acetic acid 1,2′-lactone and dl{2′α-hydroxy-4′α-p-phenylbenzoyloxy-5′β-[3″β-hydroxy-4″-(m-methylphenoxy)-but-1‴(t)-en-1‴-yl]cyclopent-1′α-yl} acetic acid 1,2′-lactone;

dl{2′α-hydroxy-4′α-p-phenylbenzoyloxy-5′β-[3″α-hydroxy-4″-(p-ethoxyphenoxy)-but-1‴(t)-en-1‴-yl]cyclopent-1′α-yl} acetic acid 1,2′-lactone and dl{2′α-hydroxy-4′α-p-phenylbenzoyloxy-5′β-[3″β-hydroxy-4″-(p-ethoxyphenoxy)-but-1‴(t)-en-1‴-yl]cyclopent-1′α-yl} acetic acid 1,2′-lactone;

dl{2′α-hydroxy-4′α-p-phenylbenzoyloxy-5′β-[3″α-hydroxy-4″-(o-methylphenoxy)-but-1‴(t)-en-1‴-yl]cyclopent-1′α-yl} acetic acid 1,2′-lactone and dl{2′α-hydroxy-4′α-p-phenylbenzoyloxy-5′β-[3″β-hydroxy-4″-(o-methylphenoxy)-but-1‴(t)-en-1‴-yl]cyclopent-1′α-yl} acetic acid 1,2′-lactone;

dl{2′α-hydroxy-4′α-p-phenylbenzoyloxy-5′β-[3″α-hydroxy-4″-(m-chlorophenoxy)-but-1‴(t)-en-1‴-yl]cyclopent-1′α-yl} acetic acid 1,2′-lactone and dl{2′α-hydroxy-4′α-p-phenylbenzoyloxy-5′β-[3″β-hydroxy-4″-(m-chlorophenoxy)-but-1‴(t)-en-1‴-yl]cyclopent-1′α-yl} acetic acid 1,2′-lactone;

dl{2′α-hydroxy-4′α-p-phenylbenzoyloxy-5′β-[3″α-hydroxy-4″-(p-chlorophenoxy)-but-1‴(t)-en-1‴-yl]cyclopent-1′α-yl} acetic acid 1,2′-lactone and dl{2′α-hydroxy-4′α-p-phenylbenzoyloxy-5′β-[3″β-hydroxy-4″-(p-chlorophenoxy)-but-1‴(t)-en-1‴-yl]cyclopent-1′α-yl} acetic acid 1,2′-lactone.

In a similar manner but using the 1′R-antimeric compounds obtained in Example 13 as starting materials there are produced the corresponding 1′R-antimeric derivatives of the above-listed racemic compounds.

EXAMPLE 15

In accordance with the methods described in Examples 3, 5, 6, 8, 9, 10, 11 and 12, dl{2′α-hydroxy-4′α-p-phenylbenzoyloxy-5″β-[3″α-hydroxy-4″-(o-methylphenoxy)-but-1''(t)-en-1''-yl]cyclopent-1'α-yl} acetic acid 1,2'-lactone is converted successively into:

dl {2'α,4'α-dihydroxy-5'β-[3''α-hydroxy-4''-(o-methylphenoxy)-but-1'''(t)-en-1''-yl]cyclopent-1'α-yl} acetic acid 1,2'-lactone, dl{2'α-hydroxy-4'α-tetrahydropyranyloxy-5'β-[3''α-tetrahydropyranyloxy-4''-(o-methylphenoxy)-but-1'''(t)-en-1''-yl]cyclopent-1'α-yl} acetic acid 1,2'-lactone, dl{2'α-hydroxy-4'α-tetrahydropyranyloxy-5'β-[3''α-tetrahydropyranyloxy-4''-(o-methylphenoxy)-but-1'''(t)-en-1''-yl]cyclopent-1'α-yl} acetaldehyde 1,2'-hemiacetal, dl 6ξ,9α-dihydroxy-11α,15α-bistetrahydropyranyloxy-16-o-methylphenoxy-17,18,19,20-tetranorprost-4-yn-13-trans-enoic acid methyl ester, dl 6ξ,9α-diacetoxy-11α,15α-bistetrahydropyranyloxy-16-o-methylphenoxy-17,18,19,20tetranorprost-4-yn-13-trans-enoic acid methyl ester, dl 9α-acetoxy-11α,15α-bistetrahydropyranyloxy-16-o-methylphenoxy-17,18,19,20-tetranorprosta-4,5,13-trans-trienoic acid methyl ester, dl 9α-acetoxy-11α,15α-dihydroxy-16-o-methylphenoxy-17,18,19,20-tetranorprosta-4,5,13-trans-trienoic acid methyl ester and dl 9α,11α,15α-trihydroxy-16-o-methylphenoxy-17,18,19,20-tetranorprosta-4,5,13-trans-trienoic acid.

Similarly, the remaining compounds obtained in Example 14 are submitted successively to the procedures described in Examples 3, 5, 6, 8, 9, 10, 11 and 12 to produce as final products:

dl 9α,11α,15α-trihydroxy-16-o-trifluoromethylphenoxy-17,18,19,20-tetranorprosta-4,5,13-trans-trienoic acid, dl 9α,11α,15α-trihydroxy-16-p-trifluoromethylphenoxy-17,18,19,20-tetranorprosta-4,5,13-trans-trienoic acid, dl 9α,11α,15α-trihydroxy-16-o-bromophenoxy-17,18,19,20-tetranorprosta-4,5,13-trans-trienoic acid, dl 9α,11α,15α-trihydroxy-16-m-bromophenoxy-17,18,19,20-tetranorprosta-4,5,13-trans-trienoic acid, dl 9α,11α,15α-trihydroxy-16-o-fluorophenoxy-17,18,19,20-tetranorprosta-4,5,13-trans-trienoic acid, dl 9α,11α,15α-trihydroxy-16-m-fluorophenoxy-17,18,19,20-tetranorprosta-4,5,13-trans-trienoic acid, dl 9α,11α,15α-trihydroxy-16-p-butylphenoxy-17,18,19,20-tetranorprosta-4,5,13-trans-trienoic acid, dl 9α,11α,15α-trihydroxy-16-o-ethoxyphenoxy-17,18,19,20-tetranorprosta-4,5,13-trans-trienoic acid, dl 9α,11α,15α-trihydroxy-16-m-ethoxyphenoxy-17,18,19,20-tetranorprosta-4,5,13-trans-trienoic acid, dl 9α,11α,15α-trihydroxy-16-p-ethylphenoxy-17,18,19,20-tetranorprosta-4,5,13-trans-trienoic acid, dl 9α,11α,15α-trihydroxy-16-phenoxy-17,18,19,20-tetranorprosta-4,5,13-trans-trienoic acid, an oil, which has the following constants:

U.V. $\lambda^{MeOH}_{max}$ 220, 264, 270, 276.5 nm (log ε 3.93, 3.05, 3.20, 3.11) (ε 8500,1120,1590,1290);

I.R. $\nu^{CHCl_3}_{max}$ 3400, 1975, 1720, 1600, 1595 cm$^{-1}$;

N.M.R. $\delta^{CDCl_3}_{TMS}$ 3.85–4.03 (m, 3H, H-11,16); 4.10–4.32 (m, 1H, H-9); 4.39–4.65 (m, 1H, H-15); 5.00–5.27 (m, 2H, H-4,6); 5.08–5.23 (m, 2H, H-13,14); 6.79–7.85 (m, 5H, aromatic);

C-13 N.M.R. δ (ppm) 176.688 (C-1); 91.351 (C-4); 204.321, 204.256 (C-5); 90.083 (C-6); 72.365, 72.138 (C-9); 42.587 (C-10); 77.437 (C-11); 55.201 (C-12); 71.650, 71.130 (C-15-16);

M.S. (as methyl ester tris-trimethylsilyl ether) m/e 511 [M$^+$—(CH$_2$—O—C$_6$H$_5$)].

dl 9α,11α,15α-trihydroxy-16-o-methoxyphenoxy-17,18,19,20-tetranorprosta-4,5,13-trans-trienoic acid, dl 9α,11α,15α-trihydroxy-16-m-methoxyphenoxy-17,18,19,20-tetranorprosta-4,5,13-trans-trienoic acid, dl 9α,11α,15α-trihydroxy-16-p-methoxyphenoxy-17,18,19,20-tetranorprosta-4,5,13-trans-trienoic acid, dl 9α,11α,15α-trihydroxy-16-p-ethoxyphenoxy-17,18,19,20-tetranorprosta-4,5,13-trans-trienoic acid, dl 9α,11α,15α-trihydroxy-16-m-methylphenoxy-17,18,19,20-tetranorprosta-4,5,13-trans-trienoic acid, dl 9α,11α,15α-trihydroxy-16-p-fluorophenoxy-17,18,19,20-tetranorprosta-4,5,13-trans-trienoic acid, dl 9α,11α,15α-trihydroxy-16-o-chlorophenoxy-17,18,19,20-tetranorprosta-4,5,13-trans-trienoic acid, dl 9α,11α,15α-trihydroxy-16-m-chlorophenoxy-17,18,19,20-tetranorprosta-4,5,13-trans-trienoic acid and dl 9α,11α,15α-trihydroxy-16-p-chlorophenoxy-17,18,19,20-tetranorprosta-4,5,13-trans-trienoic acid, as well as the corresponding 15β-hydroxy isomers, and the 8R-antimeric compounds thereof.

A representative compound in the 15β-hydroxy-series is dl 9α,11α,15β-trihydroxy-16-phenoxy-17,18,19,20-tetranorprosta-4,5,13-trans-trienoic acid, an oil, which has the following physical constants:

U.V. $\lambda^{MeOH}_{max}$ 220.5, 264, 270, 276.5 nm (log. ε 3.80, 3.03, 3.14, 3.07) (ε 6300, 1070, 1380,1175);

I.R. $\nu^{CHCl_3}_{max}$ 3420, 1975, 1725, 1600, 1595 cm$^{-1}$;

N.M.R. $\delta^{CDCl_3}_{TMS}$ 3.84–4.12 (m, 3H, H-11,16); 4.15–4.35 (m, 1H, H-9); 4.42–4.85 (m, 1H, H-15); 5.02–5.27 (m, 2H, H-4,6); 5.10–5.27 (m, 2H, H-13,14); 6.28–7.38 (m, 5H, aromatic);

C-13 N.M.R.δ(ppm) 73.698, 73.016 (C-9); 42.830 (C-10); 71.098, 71.683 (C-15,16);

M.S. (as methyl ester tris-trimethylsilyl ether) m/e 511 [M$^+$—(CH$_2$—O—C$_6$H$_5$)].

EXAMPLE 16

To a solution of 20 mg. of dl 9α,11α,15α-trihydroxy-16-m-trifluoromethylphenoxy-17,18,19,20-tetranorprosta-4,5,13-trans-trienoic acid in 5 ml. of ether is added 0.5 ml. of ethereal diazomethane, maintaining the reaction mixture at room temperature for 10 minutes. The solvents and excess reagent are eliminated under vacuum and the residue is purified by t.l.c. using ethyl acetate as eluant, to afford dl 9α,11α,15α-trihydroxy-16-m-trifluoromethylphenoxy-17,18,19,20-tetranorprosta-4,5,13-trans-trienoic acid methyl ester, an oil, having the following constants:

U.V. $\lambda^{MeOH}_{max}$ 221, 274, 281 nm (log ε 3.93, 3.32, 3.27); (δ 8500, 2090, 1860);

I.R. $\nu^{CHCl_3}_{max}$ 3610, 3420, 1980, 1740, 1600 cm$^{-1}$;

N.M.R. $\delta^{CDCl_3}_{TMS}$ 3.60 (s, 3H, methyl ester); 4.80–5.23 (m, 2H, H-4,6); 5.50–5.73 (m, 2H, H-13,14); 6.97–7.37 (m, 4H, aromatic).

Likewise, from the corresponding free acid there is obtained dl 9α,11α,15β-trihydroxy-16-m-trifluoromethylphenoxy-17,18,19,20-tetranorprosta-4,5,13-trans-trienoic acid methyl ester, an oil, having the following constants:

U.V. $\lambda^{MeOH}_{max}$ 221, 274, 281 nm (log ε 3.93, 3.32, 3.27); (ε 8500, 2090, 1860);

I.R. $\nu^{CHCl_3}_{max}$ 3600, 3500, 1980, 1740, 1600 cm$^{-1}$;

N.M.R. $\delta^{CDCl_3}_{TMS}$ 3.60 (s, 3H, methyl ester); 4.83–5.30 (m, 2H, H-4,6); 5.50–5.77 (m, 2H, H-13, 14); 6.97–7.37 (m, 4H, aromatic).

In a similar manner but using diazoethane and diazopropane in place of diazomethane, the ethyl ester and propyl of dl 9α,11α,15α-trihydroxy-16-m-trifluoromethylphenoxy-17,18,19,20-tetranorprosta-4,5,13-trans-trienoic acid and dl 9α,11α,15β-trihydroxy-16-m-trifluoromethylphenoxy-17,18,19,20-tetranorprosta-4,5,13-trans-trienoic acid are obtained.

By the same method, the corresponding 8R-antimeric compounds obtained in Example 12 and the racemic and 8R-antimeric acids of Example 15 can be converted into the corresponding methyl, ethyl and propyl esters. Representative compounds thus obtained are:

dl 9α,11α,15α-trihydroxy-16-phenoxy-17,18,19,20-tetranorprosta-4,5,13-trans-trienoic acid methyl ester, dl 9α,11α,15β-trihydroxy-16-phenoxy-17,18,19,20-tetranorprosta-4,5,13-trans-trienoic acid ethyl ester, dl 9α,11α,15α-trihydroxy-16-m-chlorophenoxy-17,18,19,20-tetranorprosta-4,5,13-trans-trienoic acid propyl ester, dl 9α,11α,15α-trihydroxy-16-o-methoxyphenoxy-17,18,19,20-tetranorprosta-4,5,13-trans-trienoic acid ethyl ester, dl 9α,11α,15β-trihydroxy-16-o-methylphenoxy-17,18,19,20-tetranorprosta-4,5,13-trans-trienoic acid methyl ester, 8R-9α,11α,15α-trihydroxy-16-m-fluorophenoxy-17,18,19,20-tetranorprosta-4,5,13-trans-trienoic acid methyl ester, 8R-9α,11α,15α-trihydroxy-16-phenoxy-17,18,19,20-tetranorprosta-4,5,13-trans-trienoic acid propyl ester, 8R-9α,11α,15α-trihydroxy-16-o-fluorophenoxy-17,18,19,20-tetranorprosta-4,5,13-trans-trienoic acid propyl ester and 8R-9α,11α,15β-trihydroxy-16-o-ethoxyphenoxy-17,18,19,20-tetranorprosta-4,5,13-trans-trienoic acid ethyl ester.

EXAMPLE 17

To a stirred solution of 1.7 g. of dl {2'α-hydroxy-4'α-p-phenylbenzoyloxy-5'β-[3''-oxo-4''-(m-trifluoromethylphenoxy)-but-1''(t)-en-1''-yl]cyclopent-1'α-yl } acetic acid 1,2'-lactone in 80 ml. of anhydrous tetrahydrofuran, cooled to −78° C there is added dropwise 2.2 ml. of a 2M methylmagnesium bromide in ether, and the resulting mixture is stirred at −78° C for 50 minutes. Saturated ammonium chloride solution (20 ml) is then added and the solvent is eliminated under reduced pressure. The product is then extracted with 100 ml. of ethyl acetate and the organic extract washed with saturated sodium chloride solution (3 x 25 ml.), dried over anhydrous magnesium sulfate and evaporated to dryness under vacuum. The residue is purified by thin layer chromatography, using methylene chloride:ethyl acetate (1:1) as eluant, thus obtaining 600 mg. of dl{2'α-hydroxy-4'α-p-phenylbenzoyloxy-5'β-[3''ξ-hydroxy-3''ξ-methyl-4''-(m-trifluoromethylphenoxy)-but-1''(t)-en-1''-yl]cyclopent-1'α-yl} acetic acid 1,2'-lactone, (racemic XII, $R^{1'}$ = Me, $R^2$ = m-CF$_3$), an oil, which has the following constants:

U.V. $\lambda_{max}^{MeOH}$ 274 nm (log ε 4.35) (ε 22,400);

I.R. $\nu_{max}^{CHCl_3}$ 3600, 3460, 1780, 1720, 1615 cm$^{-1}$;

N.M.R. $\delta_{TMS}^{CDCl_3}$ 1.35 (s, 3H, H-methyl 3''C); 2.00–3.10 (m, 6H, H-2,1', 3', 5'); 3.77 (s, 2H, H-4''); 4.83–5.40 (m, 2H, H-2', 4'); 5.67–5.80 (m, 2H, H-1'',2''); 6.90–8.07 (m, 13H, aromatic).

In a similar manner but using ethylmagnesium bromide in place of methylmagnesium bromide there is obtained dl{2'α-hydroxy-4'α-p-phenylbenzoyloxy-5'β-[3''ξ-hydroxy-3''ξ-ethyl-4''-(m-trifluoromethylphenoxy)-but-1''(t)-en-1''-yl] cyclopent-1'α-yl} acetic acid 1,2'-lactone (racemic XII, $R^1$ = Et, $R^2$ = m-CF$_3$).

Likewise 1'R-{2'α-hydroxy-4'α-p-phenylbenzoyloxy-5'β-[3''-oxo-4''-(m-trifluoromethylphenoxy)-but-1''(t)-en-1''-yl]cyclopent-1'α-yl} acetic acid 1,2'-lactone is converted into 1'R-{2'α-hydroxy-4'α-p-phenylbenzoyloxy-5'β-[3''ξ-hydroxy-3''ξ-methyl-4''-(m-trifluoromethylphenoxy)-but-1''(t)-en-1''-yl]cyclopent-1'α-yl acetic acid} 1,2'-lactone and 1'R-{2'α-hydroxy-4'α-p-phenylbenzoyloxy-5'β-[3''-hydroxy-3''ξ-ethyl-4''-(m-trifluoromethylphenoxy)-but-1''(t)-en-1''-yl] cyclopent-1'α-yl} acetic acid 1,2'-lactone.

EXAMPLE 18

A stirred solution of 500 mg. of dl{2'α-hydroxy-4'α-p-phenylbenzoyloxy-5'β-[3''ξ-hydroxy-3''ξ-methyl-4''-(m-trifluoromethylphenoxy)-but-1''(t)-en-1''-yl]cyclopent-1'α-yl} acetic acid 1,2'-lactone in 10 ml. of anhydrous toluene is cooled to −78° C under an atmosphere of argon and treated with 4 ml. of a (1:3) mixture of diisobutylaluminum hydridetoluene, and the resulting mixture is stirred at said temperature for 20 minutes. The excess reagent is then destroyed by carefully adding a few drops of methanol, and the mixture is allowed to warm to room temperature, diluted with 50 ml. of ether and 50 ml. of ethyl acetate, stirring the resulting mixture until a precipitate is formed. The solid material is separated by filtration through Celite (diatomaceous earth and the filtrate evaporated to dryness under reduced pressure. The oily residue is purified by thin layer chromatography on silica gel using ethyl acetate as gradient, to yield 205 mg. of dl{2'α,4'α-dihydroxy-5'β-[3''ξ-hydroxy-3''ξ-methyl-4''-(m-trifluoromethylphenoxy)-but-1''(t)-en-1''-yl]cyclopent-1'α-yl} acetaldehyde 1,2'-hemiacetal (racemic XIII, $R^1$ = Me, $R^2$ = m-CF$_3$), an oil, having the following constants:

U.V. $\epsilon_{max}^{MeOH}$ 222, 274, 282 nm (log ε 3190, 3.32, 3.27) (ε 7950, 2090, 1860);

I.R. $\nu_{max}^{CHCl_3}$ 3620, 3420, 1600 cm$^{-1}$;

N.M.R. $\delta_{TMS}^{CDCl_3}$ 1.20 (s, 3H, H-methyl at C-3''); 1.70–2.90 (m, 6H, H-2,1', 3',5'); 3.83 (s, 2H, H-4''); 4.40–4.70 (m, 1H, H-4'); 5.32–5.77 (m, 3H, H-1, 1'',2''); 6.83–7.40 (m, 4H, aromatic).

By the same method, dl{2'α-hydroxy-4'α-p-phenylbenzoyloxy-5'β-[3''ξ-hydroxy-3''ξ-ethyl-4''-(m-trifluoromethylphenoxy)-but-1''(t)-en-1''-yl]cyclopent-1'α-yl} acetic acid 1,2'-lactone is converted into dl{2'α,4'α-dihydroxy-5'β-[3''ξ-hydroxy-3''ξ-ethyl-4''-(m-trifluoromethylphenoxy)-but-1''(t)-en-1''-yl]cyclopent-1'α-yl} acetaldehyde 1,2'-hemiacetal (racemic XIII, $R^{1'}$ = Et, $R^2$ = m-CF$_3$).

In a similar manner but using 1'R-{2'α-hydroxy-4'α-p-phenylbenzoyloxy-5'β-[3'' ξ-hydroxy-3''ξ-methyl-4''-(m-trifluoromethylphenoxy)-but-1''(t)-en-1''-yl]cyclopent-1'α-yl} acetic acid 1,2'-lactone and 1'R-{2'α-hydroxy-4'α-p-phenylbenzoyloxy-5'β-[3''ξ-hydroxy-3 ξ-ethyl-4''-(m-trifluoromethylphenoxy)-but-1''(t)-en-1''-yl]cyclopent-1'α-yl} acetic acid 1,2'-lactone as starting materials there are obtained 1'R-{2'α,4'α-dihydroxy-5'β-[3''ξ-hydroxy-3''ξ-methyl-4''-(m-trifluoromethylphenoxy)-but-1''(t)-en-1''-yl]cyclopent-1'α-yl} acetaldehyde 1,2'-hemiacetal and 1'R-{2'α,4'α-dihydroxy-5'β-[3''ξ-hydroxy-3''ξ-ethyl-4''-(m-trifluoromethylphenoxy)-but-1''(t)-en-1''-yl]cyclopent-1′α-yl} acetaldehyde 1,2′-hemiacetal, respectively.

EXAMPLE 19

A mixture of 5 ml. of anhydrous ether, 0.721 ml. of anhydrous diisopropylamine and 0.893 ml. of anhydrous hexamethylphosphoramide is cooled to −10° C under argon atmosphere and to the cold, stirred mixture is added dropwise 2.71 ml. of a 1.9M solution of methyllithium in ether. The reaction mixture is stirred for about 10 minutes under the same conditions, it is then cooled to −78° C and treated dropwise with a solution of 252 mg. of 4- pentynoic acid in 7 ml. of anhydrous ether. When the addition is complete the temperature of the reaction mixture is aallowed to attain room temperature and maintained for 3 hours further. A solution of 100 mg. of dl {2′α,4′α-dihydroxy-5′β-[3‴}-hydroxy-3‴-methyl-4″-(m-trifluoromethylphenoxy)-but-1‴(t)-en-1‴-yl]cyclopent-1′α-yl} acetaldehyde 1,2′-hemiacetal in 15 ml. of anhydrous ether is then added, and thereafter 3.57 ml. of anhydrous hexamethylphosphoramide. The resulting reaction mixture is stirred for 40 hours at room temperature and then diluted with 25 ml. of water and extracted with methylene chloride (3 × 15 ml.) to eliminate the neutral products. The aqueous phase is saturated with sodium potassium tartrate, 200 mg. of oxalic acid dissolved in 5 ml. of water are added and the product is extracted with ethyl acetate (3 × 60 ml.). The combined organic extract is washed with saturated sodium potassium tartrate solution (3 × 15 ml.), dried over anhydrous magnesium sulfate and evaporated to drynesss under vacuum. The residue is treated with an excess of ethereal diazomethane for 15 minutes and evaporated to dryness. The residue is purified by t.l.c. using ethyl acetate as eluant, to produce 75 mg. of the pure dl 6¦,9α,11α,15¦-tetrahydroxy-15 ¦-methyl-16-m-trifluoromethylphenoxy-17,18,19,20-tetranorprost-4-yn-13-trans-enoic acid methyl ester (racemic XIV, $R^{1\prime}$ = Me, $R^2$ = m-CF$_3$), an oil, having the following constants:

U.V. $\lambda_{max}^{MeOH}$ 222, 275, 282 nm (log ε 3.92, 3.32, 3.28) (ε 8320, 2090, 1910);
I.R. $\nu_{max}^{CHCl_3}$ 3620, 3480, 1745, 1600 cm$^{-1}$;
N.M.R. $\delta_{TMS}^{CDCl_3}$ 1.40 (s, 3H, H-methyl at C-15); 2.47 (s, 4H, H-2,3); 3.62 (s, 3H, H-methyl ester); 3.83 (s, 2H, H-16); 4.10–4.60 (m, 3H, H-6,9,11); 5.57–5.73 (m, 2H, H-13,14); 6.97–7.13 (m, 4H, aromatic).

By the same method, dl {2′α,4′α-dihydroxy-5′β-[3′λ ′¦-hydroxy-3‴-ethyl-4″-(m-trifluoromethylphenoxy)-but-1‴(t)-en-1‴-yl]cyclopent-1′α-yl} acetaldehyde 1,2′-hemiacetal is converted into dl 6 ,9α,11α,15¦-tetrahydroxy-15 -ethyl-16-m-trifluoromethylphenoxy-17,18,19,20-tetranorprost-4-yn-13-trans-enoic acid methyl ester (racemic XIV, $R^{1\prime}$ = Et, $R^2$ = m-CF$_3$).

Likewise but using 1′R {2′α,4′α-dihydroxy-5′β-[3″ -hydroxy-3″¦-methyl-4″-(m-trifluoromethylphenoxy)-but-1‴(t)-en-1‴-yl]cyclopent-1′α-yl} acetaldehyde 1,2′-hemiacetal and 1′R-{2′α,4′α-dihydroxy-5′β-[3″¦-hydroxy-3″¦-ethyl-4″-(m-trifluoromethylphenoxy)-but-1‴(t)-en-1‴-yl]cyclopent-1′α-yl} acetaldehyde 1,2′-hemiacetal as starting materials there are respectively obtained 8R-6¦,9α,11α,15¦-tetrahydroxy-¦15 -methyl-16-m-trifluoromethylphenoxy-17,18,19,20-tetranorprost-4-yn-13-trans-enoic acid methyl ester and 8R-6¦,9α,11α,15¦-tetrahydroxy-15¦-ethyl-16-m-trifluoromethylphenoxy-17,18,19,20-tetranorprost-4-yn-13-trans-enoic acid methyl ester.

EXAMPLE 20

A solution of 75 mg. of dl 6¦,9α,11α,15¦-tetrahydroxy-15¦-methyl-16-m-trifluoromethylphenoxy-17,18,19,20-tetranorprost-4-yn-13-trans-enoic acid methyl ester in 0.5 ml. of pyridine and 0.15 ml. of acetic anhydride is kept at room temperature for 3 hours and 45 minutes. The reaction mixture is then poured into water and extracted with methylene chloride. The combined extracts are washed with saturated sodium chloride solution, dried over anhydrous magnesium sulfate and evaporated to dryness under reduced pressure. Purification of the residue by t.l.c. using methylene chloride:diethyl ether (8:2) as eluant, affords 78 mg. of dl 6¦,9α,11α-triacetoxy-15¦-hydroxy-15¦-methyl-16-m-trifluoromethylphenoxy-17,18,19,20-tetranorprost-4-yn-13-trans-enoic acid methyl ester (racemic XV, $R^{1\prime}$ = Me, $R^2$ = m-CF$_3$), an oil, which has the following constants:

U.V. $\lambda_{max}^{MeOH}$ 222, 275, 283 nm (log ε 3.95, 3.35, 3.27) (ε 8920, 2240, 1860);
I.R. $\nu_{max}^{CHCl_3}$ 2230, 1745, 1600 cm$^{-1}$;
N.M.R. $\delta_{TMS}^{CDCl_3}$ 1.40 (s, 3H, H-15 methyl); 1.90–2.10 (m, 9H, H-acetate); 2.47 (s, 4H, H-2,3); 3.63 (s, 3H, methyl ester); 3.83 (s, 2H, H-16); 4.67–5.50 (m, 3H, H-6,9,11); 5.60–5.77 (m, 2H, H-13,14); 7.00–7.30 (m, 4H, aromatic).

By the same method, dl 6 ,9α,11α,15 -tetrahydroxy-15¦-ethyl-16-m-trifluoromethylphenoxy-17,18,19,20-tetranorprost-4-yn-13-trans-enoic acid methyl ester is converted into dl 6¦,9α,11α-triacetoxy-15¦-hydroxy-15¦-ethyl-16-m-trifluoromethylphenoxy-17,18,19,20-tetranorprost-4-yn-13-trans-enoic acid methyl ester (racemic XV, $R^{1\prime}$ = Et, $R^2$ = m-CF$_3$).

Likewise, starting from 8R-6¦,9α,11α,15¦-tetrahydroxy-15¦-methyl-16-m-trifluoromethylphenoxy-17,18,19,20 -tetranorprost-4-yn-13-trans-enoic acid methyl ester and 8R-6¦,9α,11α,15¦-tetrahydroxy-15¦-ethyl-16-m-trifluoromethylphenoxy-17,18,19,20-tetranorprost-4-yn-13-trans-enoic acid methyl ester there are obtained 8R-6¦,9α,11α-triacetoxy-15¦-hydroxy-15¦-methyl-16-m-trifluoromethylphenoxy-17,18,19,20-tetranorprost-4-yn-13-trans-enoic acid methyl ester and 8R-6¦,9α,11α-triacetoxy-15¦-hydroxy-15¦-ethyl-16-m-trifluoromethylphenoxy-17,18,19,20-tetranorprost-4-yn-13-trans-enoic acid methyl ester, respectively.

EXAMPLE 21

A suspension of 128.5 mg. of cuprous iodide in 2.3 ml. of diethyl ether is cooled to −10°C, under argon atmosphere. To the stirred cold mixture is added, under argon atmosphere, a solution of ethereal methyllithium until the reaction mixture becomes slightly yellow. The solution is then cooled to −78°C and then a solution of 75 mg. of dl 6¦,9α,11α-triacetoxy-15¦-hydroxy-15¦-methyl-16-m-trifluoromethylphenoxy-17,18,19,20-tetranorprost-4-yn-13-trans-enoic acid methyl ester in 4 ml. of diethyl ether is added. The reaction mixture is maintained under the same conditions for 4 hours, saturated aqueous ammonium chloride solution is then added and the reaction mixture is allowed to attain room temperature. The mixture is stirred for 1 hour further, diluted with ether and filtered through Celite (diatomaceous earth). The organic layer of the filtrate is washed with saturated sodium chloride solution, dried over anhydrous magnesium sulfate and evaporated to dryness. The residue is purified by thin layer chromatography using methylene chloride:ethyl acetate (8:2) as eluant to afford 30 mg. of dl 9α,11α-diacetoxy-15ξ-hydroxy-15ξ-methyl-16-m-trifluoromethylphenoxy-17,18,19,20-tetranorprosta-4,5,13-trans-trienoic acid methyl ester (racemic XVI, R$^{1'}$ = Me, R$^2$ = m-CF$_3$), as an oil, which has the following constants:

U.V. λmax$^{MeOH}$ 224, 275, 282 nm (log ε 3.87, 3.345, 3.29) (ε 7420, 2210, 1950);
ν$_{max}$$^{CHCl_3}$ 1960, 1740, 1600 cm$^{-1}$;
N.M.R. $_{TMS}$$^{CDCl_3}$ 1.40 (s, 3H, H-methyl at C-15); 1.87–2.03 (m, 6H, acetates), 3.60 (s, 3H, H-methyl ester); 3.83 (s, 2H, H-16); 4.70–5.27 (m, 4H, H-4,6,9,11); 5.53–5.73 (m, 2H, H-13,14); 6.93–7.37 (m, 4H, aromatic).

By the same method, dl 6ξ,9α,11α-triacetoxy-15ξ-hydroxy-15ξ-ethyl-16-m-trifluoromethylphenoxy-17,18,19,20-tetranorprost-4-yn-13-trans-enoic acid methyl ester is converted into dl 9α,11α-diacetoxy-15ξ-hydroxy-15ξ-ethyl-16-m-trifluoromethylphenoxy-17,18,19,20-tetranorprosta-4,5,13-trans-trienoic acid methyl ester (racemic XVI, R$^{1'}$ = Et, R$^2$ = m-CF$_3$).

In a similar manner, starting from 8R-6ξ,9α,11α-triacetoxy-15ξ-hydroxy-15ξ-methyl-16-m-trifluoromethylphenoxy-17,18,19,20-tetranorprost-4-yn-13-trans-enoic acid methyl ester and 8R-6ξ,9α,11α-triacetoxy-15ξ-hydroxy-15ξ-ethyl-16-m-trifluoromethylphenoxy-17,18,19,20-tetranorprost-4-yn-13-trans-enoic acid methyl ester there are obtained 8R-9α,11α-diacetoxy-15ξ-hydroxy-15ξ-methyl-16-m-trifluoromethylphenoxy-17,18,19,20-tetranorprosta-4,5,13-trans-trienoic acid methyl ester and 8R-9α,11α-diacetoxy-15ξ-hydroxy-15ξ-ethyl-16-m-trifluoromethylphenoxy-17,18,19,20-tetranorprosta-4,5,13-trans-trienoic acid methyl ester, respectively.

EXAMPLE 22

To a solution of 180 mg. of dl 9α,11α-diacetoxy-15ξ-hydroxy-15ξ-methyl-16-m-trifluoromethylphenoxy-17,18,19,20-tetranorprosta-4,5,13-trans-trienoic acid methyl ester in 3.6 ml. of methanol is added a solution of 270 mg. of potassium carbonate in 1.28 ml. of water. The reaction mixture is stirred at room temperature for 115 hours and then the methanol is removed under reduced pressure. The remaining aqueous solution is diluted with 2 ml. of water and extracted with methylene chloride (3 × 10 ml.) to eliminate unsaponifiable products. The aqueous phase is saturated with solid sodium potassium tartrate and carefully acidified by the dropwise addition of a buffer citric acid-disodium hydrogen phosphate solution having a pH of 4.2, until a pH ~ 6 is reached and thereafter extracted six times with 30 ml. portions of ethyl acetate. The combined extracts are dried over anhydrous magnesium sulfate and evaporated to dryness under vacuum, to yield 115 mg. of dl 9α,11α,15-trihydroxy-15-methyl-16-m-trifluoromethylphenoxy-17,18,19,20-tetranorprosta-4,5,13-trans-trienoic acid (racemic XVII, R$^{1'}$ = Me, R$^2$ = m-CF$_3$), an oil, having the following constants:
U.V. λmax$^{MeOH}$ 223, 275, 277 nm (log. ε 3.79, 3.27, 3.23) (ε 6170, 1860, 1700);
I.R. ν$_{max}$$^{CHCl_3}$ 3600, 3420, 1980, 1725, 1600 cm$^{-1}$;
N.M.R. δ$_{TMS}$$^{CDCl_3}$ 1.41 (s, 3H, 15-CH$_3$); 3.85 (s, 2H-16); 5.03–5.23 (m, 2H, H-4,6); 5.60–5.75 (m, 2H, H-13,14); 7.00–7.40 (m, 4H, aromatic);
M.S. (as methyl ester tris-trimethylsilyl ether) m/e 539 (M$^+$ -trifluoromethylphenoxy).

By the same method, dl 9α,11α-diacetoxy-15ξ-hydroxy-15ξ-ethyl-16-m-trifluoromethylphenoxy-17,18,19,20-tetranorprosta-4,5,13-trans-trienoic acid methyl ester is converted into dl 9α,11α,15-trihydroxy-15-ethyl-16-m-trifluoromethylphenoxy-17,18,19,20-tetranorprosta-4,5,13-transtrienoic acid (racemic XVII, R$^1$ = Et, R$^2$ = m-CF$_3$).

In a similar manner, starting from 8R-9α,11α-diacetoxy-15ξ-hydroxy-15ξ-methyl-16-m-trifluoromethylphenoxy-17,18,19,20-tetranorprosta-4,5,13-trans-trienoic acid methyl ester and 8R-9α,11α-diacetoxy-15ξ-hydroxy-15ξ-ethyl-16-m-trifluoromethylphenoxy-17,18,19,20-tetranorprosta-4,5,13-transtrienoic acid methyl ester there are respectively obtained 8R-9α,11α,15ξ-trihydroxy-15ξ-methyl-16-m-trifluoromethylphenoxy-17,18,19,20-tetranorprosta-4,5,13-trans-trienoic acid and 8R-9α,11α,15ξ-trihydroxy-15ξ-ethyl-16-m-trifluoromethylphenoxy-17,18,19,20-tetranorprosta-4,5,13-trans-trienoic acid.

EXAMPLE 23

Example 17 is repeated using as starting materials the dl compounds obtained in Example 13 and methyl magnesium bromide as reagent, to produce, respectively:

dl {2'α-hydroxy-4'α-p-phenylbenzoyloxy-5'β-[3''ξ-hydroxy-3''ξ-methyl-4''-(o-trifluoromethylphenoxy)-but-1'''(t)-en-1'''-yl]cyclopent-1'α} acetic acid 1,2'-lactone, dl {2'α-hydroxy-4'α-p-phenylbenzoyloxy-5'β-[3''ξ-hydroxy-3''ξ-methyl-4''-(p-trifluoromethylphenoxy)-but-1'''(t)-en-1'''-yl]cyclopent-1'α-yl} acetic acid 1,2'-lactone, dl {2'α-hydroxy-4'α-p-phenylbenzoyloxy-5'β-[3''ξ-hydroxy-3''ξ-methyl-4''-(o-bromophenoxy)-but-1'''(t)-en-1'''-yl]cyclopent-1'α-yl} acetic acid 1,2'-lactone, dl {2'α-hydroxy-4'α-p-phenylbenzoyloxy-5'β-[3''ξ-hydroxy-3''ξ-methyl-4''-(m-bromophenoxy)-but-1'''(t)-en-1'''-yl]cyclopent-1'α-yl} acetic acid 1,2'-lactone, dl {2'α-hydroxy-4'α-p-phenylbenzoyloxy-5'β[3''ξ-hydroxy-3''ξ-methyl-4''-(o-fluorophenoxy)-but-1'''(t)-en-1'''-yl]cyclopent-1'α-yl} acetic acid 1,2'-lactone, dl {2'α-hydroxy-4'α-p-phenylbenzoyloxy-5'β-[3''ξ-hydroxy-3''ξ-methyl-4''-(m-fluorophenoxy)-but-1'''(t)-en-1'''-yl]cyclopent-1'α-yl} acetic acid 1,2'-lactone, dl {2'α-hydroxy-4'α-p-phenylbenzoyloxy-5'β-[3''ξ-hydroxy-3''ξ-methyl-4''-(p-butylphenoxy)-but-1'''(t)-en-1'''-yl]cyclopent-1'α-yl}acetic acid 1,2'-lactone, dl {2'α-hydroxy-4'α-p-phenylbenzoyloxy-5'β-[3''ξ-hydroxy-3''ξ-methyl-4''-(o-ethoxyphenoxy)-but-1'''(t)-en-1'''-yl]cyclopent-1'α-yl} acetic acid 1,2'-lactone, dl{2'α-hydroxy-4'α-p-phenylbenzoyloxy-5'β-[3''ξ-hydroxy-3''ξ-methyl-4''-(m-ethoxyphenoxy)-but-1'''(t)-en-1'''-yl]cyclopent-1'α-yl} acetic acid 1,2'-lactone, dl {2'α-hydroxy-4'α-p-phenylbenozyloxy-5'β-[3''ξ-hydroxy-3''ξ-methyl-4''-(p-ethylphenoxy)-but-1'''(t)-en-1'''-yl]cyclopent-1'α-yl} acetic acid 1,2'-lactone, dl{2'α-hydroxy-4'α-p-phenylbenzoyloxy-5'β[3''ξ-hydroxy-3''ξ-methyl-4''-(phenoxy)-but-1'''(t)-en-1'''-yl]cyclopent-1'α-yl}acetic acid 1,2'-lactone, dl{2'α-hydroxy-4'α-p-phenylbenzoyloxy-5'β-[3''ξ-hydroxy-3''ξ-methyl-4''-(o-methoxyphenoxy)-but- 1‴(t)-en-1‴-yl]cyclopent-1′α-yl} acetic acid 1,2′-lactone, dl{2′α-hydroxy-4′α-p-phenylbenzoyloxy-5′β-[3″ξ-hydroxy-3″ -methyl-4″-(m-methoxyphenoxy)-but-1‴(t)-en-1‴-yl]cyclopent-1′αyl} acetic acid 1,2′-lactone, dl{2′α-hydroxy-4′α-p-phenylbenzoyloxy-5′β-[3″ξ-hydroxy-3″ξ-methyl-4″-(p-methoxyphenoxy)-but-1‴(t)-en-1‴-yl]cyclopent-1′α-yl} acetic acid 1,2′-lactone, dl{2′α-hydroxy-4′α-p-phenylbenzoyloxy-5′β-[3″ξ-hydroxy-3″ξ-methyl-4″-(p-ethoxyphenoxy)-but-1‴(t)-en-1‴-yl]cyclopent-1′α-yl} acetic acid 1,2′-lactone, dl{2′α-hydroxy-4′α-p-phenylbenzoyloxy-5′β-[3″ξ-hydroxy-3″ξ-methyl-4″-(o-methylphenoxy)-but-1‴(t)-en-1‴-yl]cyclopent-1′α-yl} acetic acid 1,2′-lactone, dl{2′α-hydroxy-4′α-p-phenylbenzoyloxy-5′β-[3″ξ-hydroxy-3″ξ-methyl-4″-(m-methylphenoxy)-but-1‴(t)-en-1‴-yl]cyclopent-1′α-yl} acetic acid 1,2′-lactone, dl{2′α-hydroxy-4′α-p-phenylbenzoyloxy-5′β-[3″ -hydroxy-3″ξ-methyl-4″-(p-fluorophenoxy)-but-1‴(t)-en-1‴-yl]cyclopent-1′α-yl} acetic acid 1,2′-lactone, dl{2′α-hydroxy-4′α-p-phenylbenzoyloxy-5′β-[3″ξ-hydroxy-3″ξ-methyl-4″-(o-chlorophenoxy)-but-1‴(t)-en-1‴-yl]cyclopent-1′α-yl} acetic acid 1,2′-lactone, dl{2′α-hydroxy-4′α-p-phenylbenzoyloxy-5′β-[3″ξ-hydroxy-3″ξ-methyl-4″-(m-chlorophenoxy)-but-1‴(t)-en-1‴-yl]cyclopent-1′α-yl} acetic acid 1,2′-lactone and dl{2′α-hydroxy-4′α-p-phenylbenzoyloxy-5′β-[3″ξ-hydroxy-3″ξ-methyl-4″-)p-chlorophenoxy)-but-1‴(t)-en-1‴-yl]cyclopent-1′α-yl} acetic acid 1,2′-lactone.

In a similar manner but using the 1′R-antimeric compounds obtained in Example 13 as starting materials there are produced the corresponding 1′R-antimeric derivatives of the above-listed racemic compounds.

By the same method but using ethylmagnesium bromide as reagent there are obtained the corresponding racemic and 1′R-antimeric 3‴ξ-hydroxy-3″ξ-ethyl derivatives.

EXAMPLE 24

In accordance with the methods described in Examples 18, 19, 20, 21 and 22,{dl 2′α-hydroxy-4′α-p-phenylbenzoyloxy-5′β-[3″ξ-hydroxy-3″ξ-methyl-4″-(o-methylphenoxy)-but-1‴-(t)-en-1‴-yl]cyclopent-1′α-yl} acetic acid 1,2′-lactone is converted successively into:

dl{2′α,4′α-dihydroxy-5′β-[3″ξ-hydroxy-3″ξ-methyl-3″-(o-methylphenoxy)-but-1‴(t)-en-1‴-yl]cyclopent-1′α-yl} acetaldehyde 1,2′-hemiacetal, dl 6ξ,9α,11α,15ξ-tetrahydroxy-15ξ-methyl-16-o-methyl-phenoxy-17,18,19,20-tetranorprost-4-yn-13-trans-enoic acid methyl ester, dl 6ξ,9α,11α-triacetoxy-15ξ-hydroxy-15ξ-methyl-16-o-methylphenoxy-17,18,19,20-tetranorprost-4-yn-13-trans-enoic acid methyl ester.

dl 9α,11α-diacetoxy-15ξ-hydroxy-15ξ-methyl-16-o-methylphenoxy-17,18,19,20-tetranorprosta-4,5,13-trans-trienoic acid methyl ester and dl 9α,11α,15ξ-trihydroxy-15ξ-methyl-16-o-methylphenoxy-17,18,19,20-tetranorprosta-4,5,13-trans-trienoic acid.

Similarly, the remaining racemic 3′ξ-hydroxy-3‴ξ-methyl compounds obtained in Example 23 are submitted successively to the procedures described in Examples 18, 19, 20, 21 and 22 to produce as final products:

dl 9α,11α,15ξ-trihydroxy-15ξ-methyl-16-o-trifluoromethylphenoxy-17,18,19,20-tetranorprosta-4,5,13-trans-trienoic acid, dl 9α,11α,15ξ-trihydroxy-15ξ-methyl-16-p-trifluoromethylphenoxy-17,18,19,20-tetranorprosta-4,5,13-trans-trienoic acid, dl 9α,11α,15ξ-trihydroxy-15 -methyl-16-o-bromophenoxy-17,18,19,20-tetranorprosta-4,5,13-trans-trienoic acid, dl 9α,11α,15ξ-trihydroxy-15ξ-methyl-16-m-bromophenoxy-17,18,19,20-tetranorprosta-4,5,13-trans-trienoic acid, dl 9α,11α,15ξ-trihydroxy-15ξ-methyl-16-o-fluorophenoxy-17,18,19,20-tetranorprosta-4,5,13-trans-trienoic acid, dl 9α,11α,15ξ-trihydroxy-15ξ-methyl-16-m-fluorophenoxy-17,18,19,20-tetranorprosta-4,5,13-trans-trienoic acid, dl 9α,11α,15ξ-trihydroxy-15ξ-methyl-16-p-butyl-phenoxy-17,18,19,20-tetranorprosta-4,5,13-trans-trienoic acid, dl 9α,11α,15ξ-trihydroxy-15ξ-methyl-16-o-ethoxyphenoxy-17,18,19,20-tetranorprosta-4,5,13-trans-trienoic acid, dl 9α,11α, 15ξ-trihydroxy-15ξ-methyl-16-m-ethoxphenoxy-17,18,19,20-tetranorprosta-4,5,13-trans-trienoic acid, dl 9α,11α,15ξ-trihydroxy-15ξ-methyl-16-p-ethylphenoxy-17,18,19,20-tetranorprosta-4,5,13-trans-trienoic acid, dl 9α,11α,15ξ-trihydroxy-15ξ-methyl-16-phenoxy-17,18,19,20-tetranorprosta-4,5,13-trans-trienoic acid, dl 9α,11α,15ξ-trihydroxy-15ξ-methyl-16-o-methoxyphenoxy-17,18,19,20-tetranorprosta-4,5,13-trans-trienoic acid, dl 9α,11α,15ξ-trihydroxy-15ξ-methyl-16-m-methoxyphenoxy-17,18,19,20-tetranorprosta-4,5,13-trans-trienoic acid, dl 9α,11α,15ξ-trihydroxy-15ξ-methyl-16-p-methoxyphenoxy-17,18,19,20-tetranorprosta-4,5,13-trans-trienoic acid, dl 9α,11α,15ξ-trihydroxy-15ξ-methyl-16-p-ethoxyphenoxy-17,18,19,20-tetranorprosta-4,5,13-trans-trienoic acid, dl 9α,11α,15ξ-trihydroxy-15ξ-methyl-16-m-methylphenoxy-17,18,19,20-tetranorprosta-4,5,13-trans-trienoic acid, dl 9α,11α,15ξ-trihydroxy-15ξ-methyl-16-p-fluorophenoxy-17,18,19,20-tetranorprosta-4,5,13-trans-trienoic acid, dl 9α,11α,15ξ-trihydroxy-15ξ-methyl-16-o-chlorophenoxy-17,18,19,20-tetranorprosta-4,5,13-trans-trienoic acid, dl 9α,11α,15ξ-trihydroxy-15ξ-methyl-16-m-chlorophenoxy-17,18,19,20-tetranorprosta-4,5,13-trienoic acid, and dl 9α,11α,15ξ-trihydroxy-15 -methyl-16-p-chlorophenoxy-17,18,19,20-tetranorprosta-4,5,13-trans-trienoic acid, as well as the corresponding 8R-antimeric compounds thereof.

Likewise, but using the corresponding racemic 3″ -hydroxy-3″ξ-ethyl analogs and the 1′R-antimeric derivatives thereof as starting materials there are obtained the corresponding prostatrienoic acid derivatives. Representative compounds thus obtained are:

dl 9α,11α,15ξ-trihydroxy-15ξ-ethyl-16-phenoxy-17,18,19,20-tetranorprosta-4,5,13-trans-trienoic acid, dl 9α,11α,15ξ-trihydroxy-15ξ-ethyl-16-o-methyl-phenoxy-17,18,19,20-tetranorprosta-4,5,13-trans-trienoic acid, dl 9α,11α,15ξ-trihydroxy-15ξ-ethyl-16-m-trifluoromethyl-phenoxy-17,18,19,20-tetranorprosta-4,5,13-trans-trienoic acid, dl 9α,11α,15ξ-trihydroxy-15ξ-ethyl-16-o-fluoro-phenoxy-17,18,19,20-tetranorprosta-4,5,13-trans-trienoic acid, dl 9α,11α,15ξ-trihydroxy-15ξ-ethyl-16-m-chloro-phenoxy-17,18,19,20-tetranorprosta-4,5,13-trans-trienoic acid, dl 9α,11α,15ξ-trihydroxy-15ξ-ethyl-16-p-methoxy-phenoxy-17,18,19,20-tetranorprosta-4,5,13-trans-trienoic acid, 8R-9α,11α,15ξ-trihydroxy-15ξ-ethyl-16-o-methyl-phenoxy-17,18,19,20-tetranorprosta-4,5,13-trans-trienoic acid, 8R-9α,11α,15ξ-trihydroxy-15ξ-ethyl-16-p-trifluoromethylphenoxy-17,18,19,20-tetranorprosta-4,5,13-trans-trienoic acid, 8R-9α,11α,15ξ-trihydroxy-15ξ-ethyl-16-p-ethyl-phenoxy-17,18,19,20-tetranorprosta-4,5,13-trans-trienoic acid, 8R-9α,11α,15ξ-trihydroxy-15ξ-ethyl-16-o-chloro-phenoxy-17,18,19,20-tetranorprosta-4,5,13-trans-trienoic acid and 8R-9α,11α,15ξ-trihydroxy-15ξ-ethyl-16-m-fluoro-phenoxy-17,18,19,20-tetranorprosta-4,5,13-trans-trienoic acid.

EXAMPLE 25

By following the method of Example 16, dl 9α,11α,15ξ-trihydroxy-15ξ-methyl-16-m-trifluoromethylphenoxy-17,18,19,20-tetranorprosta-4,5,13-trans-trienoic acid is converted into dl 9α,11α,15ξ-trihydroxy-15ξ-methyl-16-m-trifluoromethylphenoxy-17,18,19,20-tetranorprosta-4,5,13-trans-trienoic acid methyl ester, an oil, having the following constants:

U.V. $\lambda_{max}^{MeOH}$ 223.5, 275, 281.5 nm (log ε 3.86, 3.34, 3.30) (ε 7250, 2180, 2000);

I.R. $\nu_{max}^{CHCl_3}$ 3600, 3430, 1980, 1740, 1600 cm$^{-1}$;

N.M.R. $\delta_{TMS}^{CDCl_3}$ 1.43 (s, 3H, H-15); 3.65 (s, 3H, methyl ester); 3.87 (s, 2H, H-16); 4.00–4.42 (m, 2H, H-9,11); 4.95–5.35 (m, 2H, H-4,6); 5.50–5.80 (m, 2H, H-13,14); 6.90, 7.43 (m, 4H, aromatic).

In a similar manner but using diazoethane and diazopropane as reagents there are obtained dl 9α,11α,15ξ-trihydroxy-15ξ-methyl-16-m-trifluoromethylphenoxy-17,18,19,20-tetranorprosta-4,5,13-trans-trienoic acid ethyl ester and dl 9α,11α,15ξ-trihydroxy-15ξ-methyl-16-m-trifluoromethylphenoxy-17,18,19,20-tetranorprosta-4,5,13-trans-trienoic acid propyl ester.

By the same method, the free racemic and 8R-antimeric prostatrienoic acid derivatives obtained in Example 24 can be converted into the corresponding alkyl esters. Representative compounds thus obtained are:

dl 9α,11α,15-trihydroxy-15ξ-methyl-16-o-methyl-phenoxy-17,18,19,20-tetranorprosta-4,5,13-trans-trienoic acid methyl ester, dl 9α,11α,15ξ-trihydroxy-15ξ-ethyl-16-m-trifluoromethylphenoxy-17,18,19,20-tetranorprosta-4,5,13-trans-trienoic acid ethyl ester, dl 9α,11α,15ξ-trihydroxy-15ξ-methyl-16-m-chlorophenoxy-17,18,19,20-tetranorprosta-4,5,13-trans-trienoic acid methyl ester, dl 9α,11α,15ξ-trihydroxy-15ξ-methyl-16-o-fluorophenoxy-17,18,19,20-tetranorprosta-4,5,13-trans-trienoic acid propyl ester, dl 9α,11α,15ξ-trihydroxy-15ξ-methyl-16-phenoxy-17,18,19,20-tetranorprosta-4,5,13-trans-trienoic acid methyl ester, dl 9α,11α,15ξ-trihydroxy-15-ethyl-16-p-methoxyphenoxy-17,18,19,20-tetranorprosta-4,5,13-trans-trienoic acid ethyl ester, 8R-9α,11α,15ξ-trihydroxy-15ξ-methyl-16-m-trifluoromethylphenoxy-17,18,19,20-tetranorprosta-4,5,13-trans-trienoic acid propyl ester, 8R-9α,11α,15ξ-trihydroxy-15ξ-ethyl-16-o-chlorophenoxy-17,18,19,20-tetranorprosta-4,5,13-trans-trienoic acid methyl ester, 8R-9α,11α,15ξ-trihydroxy-15ξ-methyl-16-p-butylphenoxy-17,18,19,20-tetranorprosta-4,5,13-trans-trienoic acid ethyl ester and 8R-9α,11α-15ξ-trihydroxy-15ξ-ethyl-16-m-fluorophenoxy-17,18,19,20-tetranorprosta-4,5,13-trans-trienoic acid propyl ester.

EXAMPLE 26

To a solution of 41 mg. of dl 9α,11α,15α-trihydroxy-16-m-trifluoromethylphenoxy-17,18,19,20-tetranorprosta-4,5,13-trans-trienoic acid in 10 ml. of methanol is added 1.1 molar equivalents of a 0.1N solution of sodium hydroxide and the mixture is stirred at room temperature for 1 hour. The reaction mixture is then evaporated to dryness under reduced pressure, to give the sodium salt of dl 9α,11α,15α-trihydroxy-16-m-trifluoromethylphenoxy-17,18,19,20-tetranorprosta-4,5,13-trans-trienoic acid.

By employing 1.1 molar equivalents of potassium hydroxide (in the form of a 0.1N solution) in place of sodium hydroxide in the above procedure, the potassium salt of dl 9α,11α,15α-trihydroxy-16-m-trifluoromethylphenoxy-17,18,19,20-tetranorprosta-4,5,13-trans-trienoic acid is obtained.

Similarly, the sodium and potassium salts of the other dl and 8R-antimeric prostatrienoic acid derivatives obtained in Examples 12, 15, 22 and 24, can be produced, e.g., sodium salt of dl 9α,11α,15β-trihydroxy-16-m-trifluoromethylphenoxy-17,18,19,20-tetranorprosta-4,5,13-trans-trienoic acid, sodium salt of dl 9α,11α,15α-trihydroxy-16-phenoxy-17,18,19,20-tetranorprosta-4,5,13-trans-trienoic acid, potassium salt of dl 9α,11α,15α-trihydroxy-16-p-chlorophenoxy-17,18,19,20-tetranorprosta-4,5,13-trans-trienoic acid, potassium salt of dl 9α,11α,15β-trihydroxy-16-p-butylphenoxy-17,18,19,20-tetranorprosta-4,5,13-trans-trienoic acid, sodium salt of dl 9α,11α,15ξ-trihydroxy-15ξ-methyl-16-m-trifluoromethylphenoxy-17,18,19,20-tetranorprosta-4,5,13-trans-trienoic acid, potassium salt of dl 9α,11α,15ξ-trihydroxy-15ξ-ethyl-16-phenoxy-17,18,19,20-tetranorprosta-4,5,13-trans-trienoic acid, and sodium salt of dl 9α,11α,15ξ-trihydroxy-15ξ-methyl-16-m-chlorophenoxy-17,18,19,20-tetranorprosta-4,5,13-trans-trienoic acid, as well as the corresponding 8R-antimeric compounds.

EXAMPLE 27

To a solution of 20 mg. of dl 9α,11α,15α-trihydroxy-16-m-trifluoromethylphenoxy-17,18,19,20-tetranorprosta-4,5,13-trans-trienoic acid in 5 ml. of methanol is added a mixture of 1 ml. of concentrated ammonium hydroxide solution and 2 ml. of methanol. The resulting mixture is stirred for two hours at room temperature and then evaporated to dryness, to yield the ammonium salt of dl 9α,11α,15α-trihydroxy-16-m-trifluoromethylphenoxy-17,18,19,20-tetranorprosta-4,5,13-trans-trienoic acid.

By employing dimethylamine, diethylamine or dipropylamine in place of ammonium hydroxide in the above procedure, the corresponding salts of dl 9α,11α,15α-trihydroxy-16-m-trifluoromethylphenoxy-17,18,19,20-tetranorprosta-4,5,13-trans-trienoic acid are obtained.

In a similar manner, the ammonium, dimethylamine, diethylamine and dipropylamine salts of the other racemic and 8R-antimeric prostatrienoic acid derivatives of Examples 12, 15, 22 and 24, can be prepared.

EXAMPLE 28

To a mixture of 23.6 mg. of procaine and 1.5 ml. of aqueous methanol is added 45.6 mg. of dl 9α,11α,15α-trihydroxy-16-m-trifluoromethylphenoxy-17,18,19,20-tetranorprosta-4,5,13-trans-trienoic acid in 10 ml. of methanol and the resultant reaction mixture is stirred at room temperature for 16 hours. It is then evaporated to dryness under reduced pressure to give the procaine salt of dl 9α,11α, 15α-trihydroxy-16-m-trifluoromethylphenoxy-17,18,19,20-tetranorprosta-4,5,13-trans-trienoic acid.

Similarly, the lysine, caffeine and arginine salts thereof are obtained.

In like manner, the procaine, lysine, caffeine and arginine salts of other racemic and 8R-antimeric prostatrienoic acid derivatives obtained in Examples 12, 15, 22 and 24 can be produced, e.g., the procaine salt of dl 9α,11α,15β-trihydroxy-16-m-trifluoromethylphenoxy-17,18,19,20-tetranorprosta-4,5,13-trans-trienoic acid, The caffeine salt of dl 9α,11α,15α-trihydroxy-16-phenoxy-17,18,19,20-tetranorprosta-4,5,13-trans-trienoic acid, the lysine salt of dl 9α,11α,15α-trihydroxy-16-o-methylphenoxy-17,18,19,20-tetranorprosta-4,5,13-trans-trienoic acid, the arginine salt of dl 9α,11α,15α-trihydroxy-16-o-chlorophenoxy-17,18,19,20-tetranorprosta-4,5,13-trans-trienoic acid.

the procaine salt of dl 9α,11α,15ξ-trihydroxy-15ξ-methyl-16-m-trifluoromethylphenoxy-17,18,19,20-tetranorprosta-4,5,13-trans-trienoic acid, the arginine salt of dl 9α,11α,15ξ-trihydroxy-15ξ-methyl-16-phenoxy-17,18,19,20-tetranorprosta-4,5,13-trans-trienoic acid, and the caffeine salt of dl 9α,11α,15ξ-trihydroxy-15ξ-ethyl-16-o-fluorophenoxy-17,18,19,20-tetranorprosta-4,5,13-trans-trienoic acid, as well as the corresponding 8R-antimeric compounds.

EXAMPLE 29

A solution of 12 mg. of tris(hydroxymethyl) aminomethane [NH₂—C(CH₂—OH)₃] in 0.21 ml. of water, heated to 60° C, is added with vigorous stirring to a solution of 45.6 mg. of dl 9α,11α,15α-trihydroxy-16-m-trifluoromethylphenoxy-17,18,19,20-tetranorprosta-4,5,13-trans-trienoic acid in 10 ml. of acetonitrile previously heated to about the boiling point. The flask which contained the aqueous amine solution is rinsed with three 0.05 ml. portions of water, each rinsing being added with vigorous stirring to the acetonitrile solution. The reaction mixture is then cooled to about 55° C and thereafter to room temperature. The solvent is then eliminated under vacuum and the residue crystallized from ether, to yield the tris(hydroxymethyl) aminomethane salt of dl 9α,11α,15α-trihydroxy-16-m-trifluoromethylphenoxy-17,18,19,20-tetranorprosta-4,5,13-trans-trienoic acid (tromethamine salt of dl 9α,11α,15α-trihydroxy-16-m-trifluoromethylphenoxy-17,18,19,20-tetranorprosta-4,5,13-trans-trienoic acid).

In a similar manner, dl 9α,11α,15ξ-trihydroxy-15ξ-methyl-16-m-trifluoromethylphenoxy-17,18,19,20-tetranorprosta-4,5,13-trans-trienoic acid is converted into its tromethamine salt.

What is claimed is:

1. A racemic or 8R-antimeric compound selected from the group of those represented by the following formula:

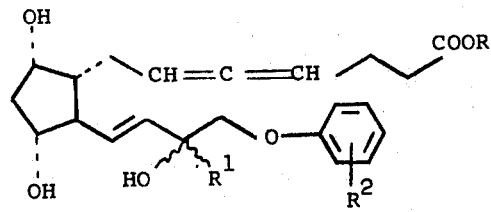

wherein R is hydrogen, a lower alkyl group of 1 to 4 carbon atoms, or the pharmaceutically acceptable, non-toxic salts of compounds in which R is hydrogen;

R¹ is hydrogen, methyl or ethyl;

R² is hydrogen, o-, m-, or p-halo (fluoro, chloro or bromo), o-, m- or p-trifluoromethyl, o-, m- or p-lower alkyl or o-, m- or p-lower alkoxy, and the wavy lines (ξ) indicate the α or β configuration or mixtures thereof, provided that when R¹ is α, the hydroxyl group, attached to the same carbon atom as R¹ is β and when R¹ is β, the hydroxyl group, attached to the same carbon atom as R¹ is α.

2. A compound according to claim 1 wherein R¹ is β-hydrogen and the hydroxyl group at C-15 is in α-configuration.

3. A compound according to claim 1 wherein R¹ is α-hydrogen and the hydroxyl group at C-15 is in β-configuration.

4. A compound according to claim 1 wherein R¹ is methyl.

5. A compound according to claim 1 wherein R¹ is ethyl.

6. A compound according to claim 2 wherein said compound is a racemate.

7. A compound according to claim 2 wherein said compound is an 8R-antimer.

8. A compound according to claim 6 wherein R is hydrogen and R² is m-trifluoromethyl, dl 9α,11α,15α-trihydroxy-16-m-trifluoromethylphenoxy-17,18,19,20-tetranorprosta-4,5,13-trans-trienoic acid.

9. A compound according to claim 6 wherein R is methyl and R² is m-trifluoromethyl, dl 9α,11α,15α-trihydroxy-16-m-trifluoromethylphenoxy-17,18,19,20-tetranorprosta-4,5,13-trans-trienoic acid methyl ester.

10. A sodium salt compound according to claim 6 wherein $R^2$ is m-trifluoromethyl, dl 9α,11α,15α-trihydroxy-16-m-trifluoromethylphenoxy-17,18,19,20-tetranorprosta-4,5,13-trans-trienoic acid sodium salt.

11. A tris(hydroxymethyl) aminomethane salt compound according to claim 6 wherein $R^2$ is m-trifluoromethyl, dl 9α,11α,15α-trihydroxy-16-m-trifluoromethylphenoxy-17,18,19,20-tetranorprosta-4,5,13-trans-trienoic acid tris(hydroxymethyl)aminomethane salt.

12. A compound according to claim 6 wherein R is hydrogen and $R^2$ is o-trifluoromethyl, dl 9α,11α,15α-trihydroxy-16-o-trifluoromethylphenoxy-17,18,19,20-tetranorprosta-4,5,13-trans-trienoic acid.

13. A compound according to claim 6 wherein R is hydrogen and $R^2$ is p-trifluoromethyl, dl 9α,11α,15α-trihydroxy-16-p-trifluoromethylphenoxy-17,18,19,20-tetranorprosta-4,5,13-trans-trienoic acid.

14. A compound according to claim 6 wherein R is hydrogen and $R^2$ is m-chloro, dl 9α,11α,15α-trihydroxy-16-m-chlorophenoxy-17,18,19,20-tetranorprosta-4,5,13-trans-trienoic acid.

15. A compound according to claim 6 wherein R is hydrogen and $R^2$ is p-chloro, dl 9α,11α,15α-trihydroxy-16-p-chlorophenoxy-17,18,19,20-tetranorprosta-4,5,13-trans-trienoic acid.

16. A compound according to claim 6 wherein R is hydrogen and $R^2$ is o-fluoro, dl 9α,11α,15α-trihydroxy-16-o-fluorophenoxy-17,18,19,20-tetranorprosta-4,5,13-trans-trienoic acid.

17. A compound according to claim 6 wherein R is hydrogen and $R^2$ is m-fluoro, dl 9α,11α,15α-trihydroxy-16-m-fluorophenoxy-17,18,19,20-tetranorprosta-4,5,13-trans-trienoic acid.

18. A compound according to claim 6 wherein R is hydrogen and $R^2$ is m-bromo, dl 9α,11α,15α-trihydroxy-16-m-bromophenoxy-17,18,19,20-tetranorprosta-4,5,13-trans-trienoic acid.

19. A compound according to claim 6 wherein R is hydrogen and $R^2$ is o-methyl, dl 9α,11α,15α-trihydroxy-16-o-methylphenoxy-17,18,19,20-tetranorprosta-4,5,13-trans-trienoic acid.

20. A compound according to claim 6 wherein R is hydrogen and $R^2$ is m-methyl, dl 9α,11α,15α-trihydroxy-16-m-methylphenoxy-17,18,19,20-tetranorprosta-4,5,13-trans-trienoic acid.

21. A compound according to claim 6 wherein R is hydrogen and $R^2$ is o-methoxy, dl 9α,11α,15α-trihydroxy-16-o-methoxyphenoxy-17,18,19,20-tetranorprosta-4,5,13-trans-trienoic acid.

22. A compound according to claim 6 wherein R is hydrogen and $R^2$ is m-methoxy, dl 9α,11α,15α-trihydroxy-16-m-methoxyphenoxy-17,18,19,20-tetranorprosta-4,5,13-trans-trienoic acid.

23. A compound according to claim 6 wherein R is hydrogen and $R^2$ is p-ethyl, dl 9α,11α,15α-trihydroxy-16-p-ethylphenoxy-17,18,19,20-tetranorprosta-4,5,13-trans-trienoic acid.

24. A compound according to claim 6 wherein R and $R^2$ are hydrogen, dl 9α,11α,15α-trihydroxy-16-phenoxy-17,18,19,20-tetranorprosta-4,5,13-trans-trienoic acid.

25. A compound according to claim 3 wherein said compound is a racemate.

26. A compound according to claim 3 wherein said compound is an 8R-antimer.

27. A compound according to claim 25 wherein R is hydrogen and $R^2$ is m-trifluoromethyl, dl 9α,11α,15β-trihydroxy-16-m-trifluoromethylphenoxy-17,18,19,20-tetranorprosta-4,5,13-trans-trienoic acid.

28. A compound according to claim 25 wherein R is methyl and $R^2$ is m-trifluoromethyl, dl 9α,11α,15β-trihydroxy-16-m-trifluoromethylphenoxy-17,18,19,20-tetranorprosta-4,5,13-trans-trienoic acid methyl ester.

29. A compound according to claim 25 wherein R and $R^2$ are hydrogen, dl 9α,11α,15β-trihydroxy-16-phenoxy-17,18,19,20-tetranorprosta-4,5,13-trans-trienoic acid.

30. A compound according to claim 4 wherein said compound is a racemate.

31. A compound according to claim 4 wherein said compound is an 8-R-antimer.

32. A compound according to claim 30 wherein R is hydrogen and $R^2$ is m-trifluoromethyl, dl 9α,11α,15ξ-trihydroxy-15ξ-methyl-16-m-trifluoromethylphenoxy-17,18,19,20-tetranorprosta-4,5,13-trans-trienoic acid.

33. A compound according to claim 30 wherein R is methyl and $R^2$ is m-trifluoromethyl, dl 9α,11α,15ξ-trihydroxy-15ξ-methyl-16-m-trifluoromethylphenoxy-17,18,19,20-tetranorprosta-4,5,13-trans-trienoic acid methyl ester.

34. A sodium salt compound according to claim 30 wherein $R^2$ is m-trifluoromethyl, dl 9α,11α,15ξ-trihydroxy-15ξ-methyl-16-m-trifluoromethylphenoxy-17,18,19,20-tetranorprosta-4,5,13-trans-trienoic acid sodium salt.

35. A tris(hydroxymethyl)aminomethane salt compound according to claim 30 wherein $R^2$ is m-trifluoromethyl, dl 9α,11α,15ξ-trihydroxy-15ξ-methyl-16-m-trifluoromethylphenoxy-17,18,19,20-tetranorprosta-4,5,13-trans-trienoic acid tris(hydroxymethyl)aminomethane salt.

36. A compound according to claim 30 wherein R is hydrogen and $R^2$ is o-trifluoromethyl, dl 9α,11α,15ξ-trihydroxy-15ξ-methyl-16-o-trifluoromethylphenoxy-17,18,19,20-tetranorprosta-4,5,13-trans-trienoic acid.

37. A compound according to claim 30 wherein R is hydrogen and $R^2$ is p-trifluoromethyl, dl 9α,11α,15ξ-trihydroxy-15ξ-methyl-16-p-trifluoromethylphenoxy-17,18,19,20-tetranorprosta-4,5,13-trans-trienoic acid.

38. A compound according to claim 30 wherein R is hydrogen and $R^2$ is m-chloro, dl 9α,11α,15ξ-trihydroxy-15ξ-methyl-16-m-chlorophenoxy-17,18,19,20-tetranorprosta-4,5,13-trans-trienoic acid.

39. A compound according to claim 30 wherein R is hydrogen and $R^2$ is p-chloro, dl 9α,11α,15ξ-trihydroxy-15ξ-methyl-16-p-chlorophenoxy-17,18,19,20-tetranorprosta-4,5,13-trans-trienoic acid.

40. A compound according to claim 30 wherein R is hydrogen and $R^2$ is o-fluoro, dl 9α,11α,15ξ-trihydroxy-15ξ-methyl-16-o-fluorophenoxy-17,18,19,20-tetranorprosta-4,5,13-trans-trienoic acid.

41. A compound according to claim 30 wherein R is hydrogen and $R^2$ is m-fluoro, dl 9α,11α,15ξ-trihydroxy-15ξ-methyl-16-m-fluorophenoxy-17,18,19,20-tetranorprosta-4,5,13-trans-trienoic acid.

42. A compound according to claim 30 wherein R is hydrogen and $R^2$ is m-bromo, dl 9α,11α,15ξ-trihydroxy-15ξ-methyl-16-m-bromophenoxy-17,18,19,20-tetranorprosta-4,5,13-trans-trienoic acid.

43. A compound according to claim 30 wherein R is hydrogen and $R^2$ is o-methyl, dl 9α,11α,15ξ-trihydroxy-15ξ-methyl-16-o-methylphenoxy-17,18,19,20-tetranorprosta-4,5,13-trans-trienoic acid.

44. A compound according to claim 30 wherein R is hydrogen and $R^2$ is m-methyl, dl 9α,11α,15ξ-trihydroxy-15ξ-methyl-16-m-methylphenoxy-17,18,19,20-tetranorprosta-4,5,13-trans-trienoic acid.

45. A compound according to claim 30 wherein R is hydrogen and $R^2$ is o-methoxy, dl 9α,11α,15ξ-trihydroxy-15ξ-methyl-16-o-methoxyphenoxy-17,18,19,20-tetranorprosta-4,5,13-trans-trienoic acid.

46. A compound according to claim 30 wherein R is hydrogen and $R^2$ is m-methoxy, dl 9α,11α,15ξ-trihydroxy-15ξ-methyl-16-m-methoxyphenoxy-17,18,19,20-tetranorprosta-4,5,13-trans-trienoic acid.

47. A compound according to claim 30 wherein R is hydrogen and $R^2$ is p-ethyl, dl 9α,11α,15ξ-trihydroxy-15ξ-methyl-16-p-ethylphenoxy-17,18,19,20-tetranorprosta-4,5,13-trans-trienoic acid.

48. A compound according to claim 30 wherein R and $R^2$ are hydrogen, dl 9α,11α,15ξ-trihydroxy-15ξ-methyl-16-phenoxy-17,18,19,20-tetranorprosta-4,5,13-trans-trienoic acid.

* * * * *

UNITED STATES PATENT OFFICE
CERTIFICATE OF CORRECTION

Patent No. 3,985,791     Dated  October 12, 1976

Inventor(s)  JOSEPH M. MUCHOWSKI et al

It is certified that error appears in the above-identified patent and that said Letters Patent are hereby corrected as shown below:

In the abstract, line 10, "15 -trihydroxy-15 -" should read --- 15ξ-trihydroxy-15ξ- ---. Column 1, line 66, "prostaglanin" should read --- prostaglandin ---. Column 13, line 4, "phenoxyl" should read --- phenoxy ---. Column 13, line 8, "15 -" should read --- 15ξ- ---. Column 16, line 14, "followng" should read --- following ---. Column 18, line 3, "$\Gamma_{TMS}^{CDCl3}$" should read --- $\delta_{TMS}^{CDCl_3}$ ---. Column 18, line 12, "1'β-yl" should read --- 1'α-yl ---. Column 21, lines 53 and 54, "[3'λ'α-" should read --- [3"α- ---. Column 22, line 23, "$\epsilon_{max}^{MeOH}$" should read --- $\lambda_{max}^{MeOH}$ ---. Column 22, lines 33 and 34, "[3'λ'β-" should read --- [3"β- ---. Column 28, line 39, "butl" should read --- but-1 ---. Column 30, line 43, o-methylphenoxy" should read o-chlorophenoxy ---. Column 30, line 45, "hydroxy" should read --- hydroxy ---. Column 30, line 46, "o-methoxylphenoxy" should read --- o-chlorophenoxy ---. Column 31, line 18, "20tet" should read --- 20-tet ---. Column 35, lines 49 and 50, "[3'λ'ξ -hydroxy" should read --- [3"ξ-hydroxy ---. Column 35, line 56, "[3" -hydroxy" should read --- [3"ξ-hydroxy ---. Column 35, line 63, "-ξ15 -" should read --- 15ξ- ---. Column 36, line 28, "6 , 9α" should read --- 6ξ, 9α --- and "15 -" should read --- 15ξ- ---. Column 37, line 10, "cm $^1$, " should read --- cm$^{-1}$; ---. Column 37, line 57, "15 -trihydroxy-15 -methyl" should read --- 15ξ-trihydroxy-15ξ-methyl ---. Column 38, lines 4, 5 and 6, "15-trihydroxy-15 ethyl" should read --- 15ξ-trihydroxy-15ξ-ethyl --- "transtrienoic" should read --- trans-trienoic ---. Column 39, line 4, "3" -" should read --- 3"ξ -methyl ---. Column 39, line 5, "αyl " should read --- α-yl ---. Column 39, line 55, " -3"-" should read --- -4"- ---. Column 40, line 66, "3" - should read --- 3"ξ- ---. Column 41, line 63, "15 -" should read 15ξ- ---. Column 42, line 10, "15 -" should read --- 15ξ- ---. Column 43, lines 15 and 16, "9α,1-1α," should read --- 9α,11α, ---. Claim 8, Column 44, line 62, "dl" should

UNITED STATES PATENT OFFICE
CERTIFICATE OF CORRECTION

Patent No. 3,985,791             Dated October 12, 1976

Inventor(s) JOSEPH M. MUCHOWSKI et al

It is certified that error appears in the above-identified patent and that said Letters Patent are hereby corrected as shown below:

read --- dl ---.  Claim 11, Column 45, lines 9 and 10, "methyl-)" should read --- methyl) ---.  Claim 16, Column 45, line 28, "dl" should read --- dl ---.  Claim 31, Column 46, line 14, "8-R-" should read --- 8R- ---.

Signed and Sealed this

Fifteenth Day of November 1977

[SEAL]

Attest:

RUTH C. MASON
*Attesting Officer*

LUTRELLE F. PARKER
*Acting Commissioner of Patents and Trademarks*